United States Patent
Nakata

(10) Patent No.: US 9,896,713 B2
(45) Date of Patent: Feb. 20, 2018

(54) METHOD FOR DETERMINING SITE HAVING N-LINKED SUGAR CHAIN ADDED THERETO OR PROPORTION OF SAID ADDITION

(71) Applicant: TOSOH CORPORATION, Shunan-shi, Yamaguchi (JP)

(72) Inventor: Daisuke Nakata, Ayase (JP)

(73) Assignee: TOSOH CORPORATION, Shunan-shi, Yamaguchi (JP)

(*) Notice: Subject to any disclaimer, the term of this patent is extended or adjusted under 35 U.S.C. 154(b) by 0 days.

(21) Appl. No.: 15/108,143

(22) PCT Filed: Dec. 17, 2014

(86) PCT No.: PCT/JP2014/083449
§ 371 (c)(1),
(2) Date: Jun. 24, 2016

(87) PCT Pub. No.: WO2015/098663
PCT Pub. Date: Jul. 2, 2015

(65) Prior Publication Data
US 2016/0319323 A1 Nov. 3, 2016

(30) Foreign Application Priority Data

Dec. 25, 2013 (JP) .................. 2013-267826

(51) Int. Cl.
*C12Q 1/34* (2006.01)
*C12N 9/80* (2006.01)
*C07K 14/57* (2006.01)
*G01N 33/68* (2006.01)

(52) U.S. Cl.
CPC ............ *C12Q 1/34* (2013.01); *C07K 14/57* (2013.01); *C12N 9/80* (2013.01); *C12Y 305/01052* (2013.01); *G01N 33/6866* (2013.01); *G01N 2333/57* (2013.01); *G01N 2333/98* (2013.01); *G01N 2440/38* (2013.01)

(58) Field of Classification Search
None
See application file for complete search history.

(56) References Cited

U.S. PATENT DOCUMENTS

| | | |
|---|---|---|
| 2006/0216766 A1 | 9/2006 | Rye |
| 2009/0187011 A1 | 7/2009 | Nishimura et al. |
| 2013/0288272 A1 | 10/2013 | Narimatsu et al. |

FOREIGN PATENT DOCUMENTS

| | | |
|---|---|---|
| EP | 2 617 730 A1 | 7/2013 |
| JP | 2006-61019 A | 3/2006 |
| JP | 2006-517664 A | 7/2006 |
| WO | 2004/070389 A1 | 8/2004 |
| WO | 2008/001888 A1 | 1/2008 |
| WO | 2012/036094 A1 | 3/2012 |

OTHER PUBLICATIONS

Yoshimi Kanie et al., "Insight into the Regulation of Glycan Synthesis in *Drosophila* Chaoptin Based on Mass Spectrometry", PLoS One, May 2009, pp. 1-13, vol. 4, Issue 5, #e5434.
Ulla-Maja Bailey et al., "Deglycosylation systematically improves N-glycoprotein identification in liquid chromatography-tandem mass spectrometry proteomics for analysis of cell wall stress responses in *Saccharomyces cerevisiae* lacking Alg3P", Journal of Chromatography B, 2013, pp. 16-21, vol. 923-924.
International Search Report for PCT/JP2014/083449 dated Mar. 24, 2015.
Soowannayan et al., "Glycosylation of gp116 and gp64 envelope proteins of yellow head virus of *Penaeus monodon* shrimp", Journal of General Virology, 2010, vol. 91, pp. 2463-2473.
Leonard et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells", The Journal of Biological Chemistry, Jun. 1990, vol. 265, No. 18, pp. 10373-10382.
Kaji et al., "Lectin affinity capture, isotope-coded tagging and mass spectrometry to identify N-Linked glycoproteins", Nature Biotechnology, Jun. 2003, vol. 21, No. 6, pp. 667-672.
Pan et al., "Quantitative Glycoproteomics Analysis Reveals Changes in N-Glycosylation Level Associated with Pancreatic Ductal Adenocarcinoma", Journal Proteome Research, 2014, vol. 13, pp. 1293-1306 (34 pages total).

*Primary Examiner* — Lisa V Cook
(74) *Attorney, Agent, or Firm* — Sughrue Mion, PLLC

(57) ABSTRACT

A method for detecting a site which can be modified with an N-linked glycan chain and to which an N-linked glycan chain is actually linked in a glycoprotein; and a method for determining the state of an N-linked glycan chain addition at the site are provided. A glycoprotein having an N-linked glycan chain linked thereto is subjected to an N-linked glycan chain removal treatment with a peptide N-glycanase, subsequently a site capable of being modified with an N-linked glycan chain, in which an Asn residue has been changed to an Asp residue by the action of the peptide N-glycanase, is treated with an endo-type peptidase capable of recognizing an Asp residue to thereby produce peptide fragments, and subsequently the mass of the fragments is detected. In this manner, a site which can be modified with an N-linked glycan chain and to which an N-linked glycan chain is actually linked can be detected. Furthermore, the proportion or state of of the N-linked glycan chain addition at the site can be determined from the intensity of a signal generated upon the detection.

11 Claims, 11 Drawing Sheets

FIG. 2

```
  1 KESRAKKFQR  QHMDSDSSPS  SSSTYCNQMM   30
 31 RRRNMTQGRC  KPVNTFVHEP  LVDVQNVCFQ   60
 61 EKVTCKNGQG  NCYKSNSSMH  ITDCRLTNGS   90
 91 RYPNCAYRTS  PKERHIIVAC  EGSPYVPVHF  120
121 DASVEDST    (SEQ ID No.2)
```

Electrophoresis image of human interferon gamma (IFNG) expressed in E.coli

Electrophoresis image of human interferon gamma (IFNG) expressed in CHO cells

METHOD FOR DETERMINING SITE HAVING N-LINKED SUGAR CHAIN ADDED THERETO OR PROPORTION OF SAID ADDITION

CROSS REFERENCE TO RELATED APPLICATIONS

This application is a National Stage of International Application No. PCT/JP2014/083449 filed Dec. 17, 2014, claiming priority based on Japanese Patent Application No. 2013-267826 filed Dec. 25, 2013, the contents of all of which are incorporated herein by reference in their entirety.

TECHNICAL FIELD

The present invention relates to a method for determining a site linked with an N-linked glycan chain or determining the proportion thereof in a glycoprotein. More particularly, the present invention relates to a method for detecting a site where an N-linked glycan chain is actually linked thereto at an N-linked glycosylation site of a glycoprotein. In addition, in the case the addition states of an N-linked glycan chain at an N-linked glycosylation site of a glycoprotein differ in each molecule, i.e., the addition states are heterogenous, the present invention relates to a method for measuring the degree of addition of an N-linked glycan chain at that site.

BACKGROUND ART

The site of a glycoprotein where an N-linked glycan chain binds can be predicted from a genetically encoded amino acid sequence, and those amino acids are referred to as an N-linked glycosylation site. In the case a protein having an ER localization signal in the manner of secretory proteins or membrane proteins has this N-linked glycosylation site, it has the possibility of being subjected to N-linked glycosylation. However, this does not mean that N-linked glycan chains are linked to all the N-linked glycosylation sites of a protein, and even in the case of the same N-linked glycosylation site of the same protein, the state (presence or absence) of the N-linked glycan chain addition may differ according to the molecule, and the state of an N-linked glycan chain addition is thought to be dependent on the conformation of the protein or type of expressing cells and the like.

Until now, several methods have been reported for investigating a site where an N-linked glycan chain is actually linked to an N-linked glycosylation site (to also be referred to an "N-linked glycosylated site"), and the N-linked glycosylated sites of various glycoproteins have been determined.

In Non-Patent Document 1, N-linked glycosylation and the structures of N-linked glycan chains at N-linked glycosylation sites were predicted during the course of determining the secondary structure of gp120, a structural protein of HIV. That method consisted of subjecting reductively alkylated gp120 glycoprotein to deglycosylation treatment with peptide N-glycanase F having diamidase activity (to be referred to as "PNGase F") or EndoH, which is a type of endo-type glycosidase, further digesting with trypsin or Asp-N and the like, isolating by reverse-phase chromatography, comparing the resulting chromatogram with a chromatogram obtained by digesting a non-deglycosylated glycoprotein with trypsin or Asp-N and the like, and judging a peptide having a prolonged elution time to have been removed of the linked N-linked glycan chain, namely judging that an N-linked glycan chain had been linked to that peptide. Non-Patent Document 1 does not disclose or suggest digesting a protein that has the same amino acid sequence as gp120 protein but does not have a glycan chain with Asp-N and the like followed by comparing the resulting peptide fragment, nor does it disclose or suggest determining the addition of an N-linked glycan chain to an Asn residue by utilizing the change of an asparagine residue having a glycan chain linked thereto to an aspartic acid residue when subjected to deglycosylation treatment with an enzyme having deamidase activity.

In addition, in Non-Patent Document 2, after carrying out fragmentation on a glycoprotein, the glycosylated peptide is recovered with lectin followed by subjecting to deglycosylation treatment with PNGase F and analyzing by LC/MS. However, there is no disclosure or suggestion whatsoever regarding specifically hydrolyzing the glycoprotein according to an Asn residue or aspartic acid residue (Asp residue).

In addition, in Non-Patent Document 3, a method for determining a site where an N-linked glycan chain has actually been linked is indicated that consists of removing an amino group of an Asn residue when subjecting a glycoprotein to deglycosylation treatment with PNGase F having deamidase activity, and utilizing the change to an Asp residue as a result thereof. More specifically, in this method, in the case a peptide fragment, obtained by deglycosylation treatment of N-linked glycan chain of a glycoprotein by PNGase F followed by fragmenting with a peptidase such as trypsin, contains an N-linked glycosylation site and has an N-linked glycan chain linked to that site, the site where an N-linked glycan chain has been linked is determined by using as an indicator an increase of one dalton in the mass of the fragment from the theoretical value thereof. However, the method of Non-Patent Document 3 does not use an enzyme that specifically hydrolyzes an Asn residue or Asp residue. In addition, this method is an effective method for determining the site were an N-linked glycan chain is actually linked in the case of a uniform addition state of N-linked glycan chains at an N-linked glycosylation site. However, in the case N-linked glycosylation is not uniform, two fragments differing in mass by one dalton may be detected in the case the resulting peptide fragment has the original Asn residue and the case in which it has changed to an Asp residue. During actual measurements, it is necessary to consider the effect of naturally-occurring isotopes, and in the case two masses are detected that differ by one dalton, it is extremely difficult to clearly distinguish between whether the difference in mass is due to the naturally-occurring isotope or a difference of one dalton attributable to the difference in mass between the Asn residue and Asp residue.

PRIOR ART DOCUMENTS

Non-Patent Documents

Non-Patent Document 1: J. Biol. Chem., 1990, 265, 10373-10382
Non-Patent Document 2: Nat. Biotechnol., 2003, 21, 677-672
Non-Patent Document 3: J. of General Virology, 2010, 91, 2463-2473

DISCLOSURE OF THE INVENTION

Problems to be Solved by the Invention

An object of the present invention is to provide a technique for determining a site on a glycoprotein where an N-linked glycan chain is linked, and to provide a method enabling to detect a state of glycan chain addition even if those state of addition are not uniform depending on each molecule.

Means for Solving the Problems

The inventor of the present invention achieved the present invention as a result of conducting extensive studies regarding the aforementioned object. Namely, the present invention is as indicated below.

(1) A method for detecting a site where an N-linked glycan chain is linked and/or a site where it is not linked in a glycoprotein, comprising:

(A) removing an N-linked glycan chain from an N-linked glycosylated glycoprotein and changing an asparagine residue to which the N-linked glycan chain is linked to an aspartic acid residue;

(B) hydrolyzing the glycoprotein obtained in step (A) specifically for the asparagine residue or aspartic acid residue to obtain peptide fragments;

(C) detecting the peptide fragments obtained in step (B); and (D) by comparing with a peptide fragment obtained by hydrolyzing in the same manner as step (B) a protein having the same amino acid sequence as the original N-linked glycosylated glycoprotein but not having a glycan chain, judging that a glycan chain is linked to an N-linked glycosylation site in the case different peptide fragments are present among the peptide fragments detected in step (C) and the different peptide fragments are presumed to contain an N-linked glycosylation site or amino acid residue adjacent thereto, and/or judging that a glycan chain is not linked to an N-linked glycosylation site in the case identical peptide fragments are present among the peptide fragments detected in step (C) and those identical peptide fragments are presumed to contain an N-linked glycosylation site.

(2) The method described in (1), wherein step (A) is carried out using a peptide N-glycanase having deamidase activity.

(3) The method described in (2), wherein the peptide N-glycanase having deamidase activity is peptide N-glycanase F or peptide N-glycanase A.

(4) The method described in any of (1) to (3), wherein step (B) is carried out using an endo-type peptidase that acts by specifically recognizing an aspartic acid residue.

(5) The method described in (4), wherein the endo-type peptidase that acts by specifically recognizing an aspartic acid residue is Asp-N or Glu-C.

(6) The method described in any of (1) to (5), wherein the detection in step (C) is carried out using a mass spectrometer.

(7) A method for detecting a site in a glycoprotein where an N-linked glycan chain is linked by using the method described in any of (1) to (6) above and determining the proportion of N-linked glycan chain linked from signal strength at the time of detection.

(8) A method for detecting a glycoprotein for which the site where an N-linked glycan chain is linked or the proportion of that addition has changed, comprising determining the sites where an N-linked glycan chain is linked, or the proportion thereof that have been linked, for a plurality of samples using the method described in any of (1) to (7), and comparing those results.

(9) A glycoprotein detected by the method described in (8), in which the site where an N-linked glycan chain is linked or the proportion of that addition differs in a comparison between a sample obtained from a patient with a disease and a sample obtained from a healthy individual.

(10) A method for detecting a disease, comprising determining the site where an N-linked glycan chain is linked or the proportion of that addition in the glycoprotein described in (9) that is present in a sample.

(11) A method for determining the site where an N-linked glycan chain is linked or the proportion of that addition in a glycoprotein present in a pharmaceutical by using the method described in any of (1) to (7) above.

The following provides a more detailed explanation of the present invention. First, an explanation is provided of a method for detecting a site where an N-linked glycan chain is actually linked in a glycoprotein.

In the present invention, a target glycoprotein is particularly not limited. The disulfide bonds of the glycoprotein are preferably reduced prior to step (A), and the thiol groups exposed as a result of reduction are preferably subjected to protective treatment by alkylation and the like prior to the peptide fragmentation treatment of step (B). Although there are no particular limitations on the sample used in the present invention, the sample is preferably in a state in which the target glycoprotein has been separated from other glycoproteins as a result of electrophoresis or column-chromatographic separation and the like. In addition, a pharmaceutical containing a glycoprotein can also be used for the sample. Furthermore, in the case the target glycoprotein is mixed with other glycoproteins in a sample, it also preferable to employ a method in which, after carrying out step (A) in the same manner as described above, step (B) is carried out on the target protein after having separated from the other glycoproteins by carrying out electrophoresis or column-chromatographic separation and the like prior to the peptide fragmentation treatment of step (B), namely between step (A) and step (B).

In step (A) of the present invention, in addition to removing N-linked glycan chain from an N-linked glycosylated glycoprotein, an Asn residue where the N-linked glycan chain is linked is changed to an Asp residue. This means that, during removal of the N-linked glycan chain from the glycoprotein, the amino group derived from an Asn residue where the N-linked glycan chain is linked is also removed. As a result, the Asn residue changes to an Asp residue. Although there are no particular limitations on the method used to carry out this step (A), an example of a preferable method consists of using a peptide N-glycanase enzyme having deamidase activity. Peptide N-glycanase enzymes having deamidase activity have an action that also removes the amino group directly linked to the N-linked glycan chain during removal of the N-linked glycan chain from the Asn residue where the N-linked glycan chain is linked, and as a result thereof, the Asn residue where the N-linked glycan chain is linked changes to an Asp residue. Although there are no particular limitations on the peptide N-glycanase enzyme having deamidase activity, examples thereof include PNGase F and peptide N-glycanase A, with PNGase F being most preferable.

Next, in step (B), the glycoprotein obtained in step (A) is specifically hydrolyzed for the Asn residue or Asp residue to obtain peptide fragments. At this time, since the original amino acid residue in the form of the Asn residue changes to an Asp residue at the N-linked glycosylation site where the N-linked glycan chain is linked, a different peptide fragment can be determined to have been formed by comparing that peptide fragment with peptide fragments obtained by similarly hydrolyzing a glycoprotein having the same amino acid sequence as the original glycoprotein but not having a glycan chain by hydrolyzing specifically for the Asn residue or Asp residue. The cleavage site varies according to the enzyme used, and the glycoprotein is cleaved at a prescribed location based on the target Asn residue or Asp residue. For example, the glycoprotein may be cleaved immediately before (N side) or immediately after (C side) the Asn residue or Asp residue. Although there are no particular limitations on the method used to specifically hydrolyze the Asn residue or Asp residue, hydrolysis is preferably carried out using an endo-type peptidase that acts by specifically recognizing an Asn residue or Asp residue. Asparaginyl endopeptidase derived from *Canavalia ensiformis* is known to be an endo-type peptidase that acts by specifically recognizing an Asn residue. Hydrolysis using an endo-type peptidase that acts by specifically recognizing an Asp residue is particularly preferable, and an endo-type peptidase such as Asp-N or Glu-C is used.

In step (B), treatment may be carried out using one or more endo-type peptidases having different specificity in order to facilitate subsequent analysis. The type of enzyme used here is determined based on sequence data of the protein or peptide to be analyzed, and is preferably an enzyme other than that which recognizes an Asp residue or Asn residue. Although there are no particular limitations on this endo-type peptidase, specific examples thereof include trypsin, chymotrypsin, Lys-C and Arg-C. Treatment with such an enzyme makes it possible to obtain shorter peptide fragments, which may facilitate detection in the subsequent step (C).

In step (C), the peptide fragments obtained in step (B) are detected. Although there are no particular limitations on the method used, the peptide fragments are preferably detected according to mass, and more specifically, a method is preferably used in which the masses of the peptide fragments formed are determined with a mass spectrometer. In this case, amino acids that compose the peptide fragments can be predicted from these masses, and if the amino acid sequence of the glycoprotein is known, the locations of the peptides in the sequence thereof can also be predicted. In addition, by carrying out tandem mass spectrometry, which is a technique for identifying a peptide sequence by using a method consisting of analyzing the amino acid composition of peptide fragments detected having a specific mass by additionally ionizing the peptide fragments, it is possible to identify peptide fragments by determining the amino acid sequence of a peptide fragmented by an endo-type peptidase.

In step (D), a glycan chain is judged to have been linked to that N-linked glycosylation site in the case of comparing with peptide fragments (I), obtained by carrying out hydrolysis treatment in the same manner as step (B) on a protein having the same amino acid sequence as the original N-linked glycosylated glycoprotein but not having a glycan chain, and it is predicted that different fragments are present among the peptide fragments (II) detected in step (C) and that the different peptide fragments contain an N-linked glycosylation site or amino acid residue adjacent thereto. Alternatively or in combination therewith, a glycan chain is judged to not be linked to that N-linked glycosylation site in the case of comparing with the peptide fragments (I), obtained by carrying out hydrolysis treatment in the same manner as step (B) on a protein having an amino acid sequence identical to the original N-linked glycosylated glycoprotein but not having a glycan chain, and it is predicted that identical fragments are present among the peptide fragments (II) detected in step (C) and that the identical peptide fragments contain an N-linked glycosylation site.

At this time, a protein having an amino acid sequence identical to the original N-linked glycosylated glycoprotein but not having a glycan chain can also refer to that having an amino acid sequence predicted from the gene sequence of that glycoprotein but does not have a glycan chain. Comparison with peptide fragments (I) obtained by hydrolyzing such a protein in the same manner as step (B) may also refer to actually carrying out hydrolysis in the same manner as step (B) and then comparing with the result of detecting the resulting peptide fragments in the same manner as step (C), and if the amino acid sequence of that protein is known, the hydrolyzed location is predicted from that sequence and the resulting peptide fragments are predicted and compared therewith.

An "N-linked glycosylation site" refers to a site of a glycoprotein where an N-linked glycan chain can bind. More specifically, this refers to the first aspartic acid residue (aspartic acid residue to be referred to as "Asn residue") of a three amino acid sequence, in the manner of Asn-Xaa-Ser or Asn-Xaa-Thr in a glycoprotein (wherein, Xaa indicates an amino acid other than proline, and both of these sequences are collectively referred to as "NXS/T" in the present description), being an N-linked glycosylation site. Furthermore, in the present invention, since the asparagine residue where the glycan chain is linked changes to an aspartic acid residue after going through step (A), in the glycoprotein or peptide fragment obtained after going through step (A), the N-linked glycosylation site refers to a site corresponding to the N-linked glycosylation site of the original glycoprotein. An amino acid sequence adjacent to the N-linked glycosylation site refers to an amino acid residue on the N side or C side of the asparagine residue serving as the N-linked glycosylation site, and in a certain aspect, cleavage can occur between the N-linked glycosylation site and amino acid residue adjacent thereto in step (B).

An overview of the method of the present invention as explained above is shown in FIG. 1. In FIG. 1, in order to simplify the explanation, an example is shown of the case of using PNGase F in step (A) and using Asp-N in step (B). Furthermore, sequences in FIG. 1 are represented with single-letter amino acid codes, and X represents an amino acid other than proline. First, an N-linked glycosylated glycoprotein (original sequence) has two N-linked glycosylation sites and only one of those sites has a glycan chain linked thereto. When this is treated with PNGase F in step (A), the N-linked glycan chain is removed and the Asn were the glycan chain is linked changes to Asp, while the Asn where a glycan chain is not linked remains as Asn. Next, when this is treated with Asp-N in step (B), cleavage by Asp-N enzyme occurs at the portion where Asn was changed to Asp by PNGase F and on the N-terminal side of the Asp originally present. As a result, four peptide fragments (pepA, pepB, pepC' and pep (D+E) (corresponding to peptide fragments (II)) are detected. On the other hand, in the case of having treated a protein having an amino acid sequence identical to the original N-linked glycosylated glycoprotein but not having a glycan chain with Asn-N, three peptide fragments (pepA, pep (B+C) and pep (D+E)) (corresponding to peptide fragments (I)) are detected. In the case of comparing these two sets of fragments and it is predicted that different fragments (pepB, pepC') are present in the fragments corresponding to peptide fragments (II) and that those different peptide fragments contain an N-linked glycosylation site or amino acid residue adjacent thereto based on the masses of the peptide fragments, an N-linked glycan chain is judged to have been linked to that N-linked glycosylation site.

In addition, according to the method of the present invention, even if the states of N-linked glycan chains addition at a certain N-linked glycosylation site are not uniform, a peptide fragment derived from an N-linked glycosylation site were the N-linked glycan chain has been linked can be clearly distinguished from a peptide fragment derived from an N-linked glycosylation site where an N-linked glycan chain has not been linked. Consequently, a site where an N-linked glycan chain has been linked can be detected even if the states of an N-linked glycan chain addition in a glycoprotein targeted for detection are not uniform.

In addition, in the present invention, a site in a glycoprotein were an N-linked glycan chain is linked can be detected according to the aforementioned method, and the proportion of N-linked glycan chain linked can be determined from the signal strength thereof.

In addition, a site where an N-linked glycan chain is linked or the proportion of that addition as described above can be determined for a plurality of samples, and a glycoprotein for which the site where an N-linked glycan chain is linked or the proportion of that addition has changed can be detected by comparing those results.

A glycoprotein for which the site where an N-linked glycan chain is linked or the proportion of that addition has changed in this manner and in which the site where the N-linked glycan chain is linked or the proportion of that addition differs in a comparison between a sample obtained from a patient with a disease and a sample obtained from a healthy individual can serve as a disease marker that provides important information in terms of detecting the disease. An example of a method used to discover such disease markers is indicated in FIG. 9. In FIG. 9, a sample for analysis is first subjected to treatment with PNGase F in step (A). Subsequently, proteins are separated by two-dimensional electrophoresis followed by extracting proteins targeted for analysis (here, proteins #1 to #4 for analyses). Subsequently, each protein for analysis is digested with Asp-N in step (B). By then carrying out mass spectrometry on the resulting peptide fragments in step (C), the peptide fragments are detected, and in the next step (D), a judgment is made of the presence or absence of the addition of a glycan chain at the N-linked glycosylation sites of the analyzed proteins. At this time, in steps (C) and (D), the analyzed proteins are identified based on information contained in a protein database, and a search is made of peptide fragments containing an N-linked glycosylation site. Finally, the glycosylation rate at each glycosylation site of each analyzed protein is determined. Furthermore, step (C) and step (D) can be incorporated as the functions of a software package for operating a mass analyzer or a software package for analyzing the results of mass spectrometry. This method is carried out on samples obtained from persons with a disease and samples obtained from healthy individuals, and those for which abnormalities are observed for both persons with a disease and healthy individuals can serve as disease marker candidates.

Accordingly, a disease can be detected by determining a site where an N-linked glycan chain is actually linked, or the proportion of that addition, at an N-linked glycosylation site of such a disease marker present in a sample. Although there are no particular limitations on the method used to detect such a disease marker, examples thereof include not only the method using a mass spectrometer as previously described, but also immunological techniques represented by such techniques as ELISA or western blotting. Examples of samples include whole blood, serum, plasma and urine.

In addition, by using the method of the present invention as described above, a site where an N-linked glycan chain is linked or the proportion of that addition can be determined at an N-linked glycosylation site of a glycoprotein in a pharmaceutical. For example, in the case of pharmaceuticals composed mainly of a glycoprotein in the manner of antibodies serving as the main component of antibody preparations, interferon beta or erythropoietin, and in which the presence or absence of a glycan chain has an effect on pharmacological efficacy, the state in which the glycan chain is linked to the protein is required to be uniform. Thus, quality control of such pharmaceuticals can be carried out using the method of the present invention.

Effects of the Invention

According to the present invention, a site which is an N-linked glycosylation site and where an N-linked glycan chain is actually linked can be detected, and the proportion of N-linked glycan chain linked to an N-linked glycosylation site can be determined. In addition, according to the present invention, this detection and determination can be carried out even if the state of the N-linked glycan chain addition is not uniform.

BRIEF DESCRIPTION OF THE DRAWINGS

FIG. 2 is a drawing showing the amino acid sequence of ribonuclease 1 (to be abbreviated as "RNase 1") as predicted from gene sequence information, and three N-linked glycosylation sites.

EXAMPLES

Example 1

Detection of N-Linked Glycosylation Site by Asp-N Digestion

Recombinant human pancreas-specific RNase 1 used for analysis was obtained by introducing the full length gene of human pancreas-specific RNase 1 (SEQ ID NO. 1) into cultured Chinese hamster ovary cells (CHO-K1 cells) in accordance with ordinary methods and purifying the recombinant protein secreted into the medium by affinity chromatography. More specifically, a gene sequence encoding human pancreas-specific RNase 1 (SEQ ID NO. 1) was inserted into a pcDNA3.1-mycHis vector (Life Technologies Corp.) to prepare a mammalian cell expression vector. The prepared mammalian cell expression plasmid was inserted into CHO-K1 cells using Lipofectamine 2000 (Life Technologies Corp.) and the human pancreas-specific RNase 1 secreted into the medium was purified using an affinity column immobilized with anti-RNase 1 antibody.

RNase 1 is a protein composed of the amino acid sequence shown in SEQ ID NO. 2, sequences thereof enabling the addition of an N-linked glycan chain (NXS/T) are present at three locations indicated with underlines in FIG. 2, and N-linked glycan chains are able to bind to the Asn residues at positions 34, 76 and 88 (referred to as "Asn34", "Asn76" and "Asn88", respectively). Recombinant RNase 1 expressed in the CHO cells used was confirmed to have a proportion of glycan chains linked to Asn88 of 8% of all Asn88 according to the method described in International Publication WO 2013/187371. Sites where N-linked glycan chains are actually linked and the degree of glycan chain addition at all N-linked glycosylation sites were determined in this sample.

Figure 1:
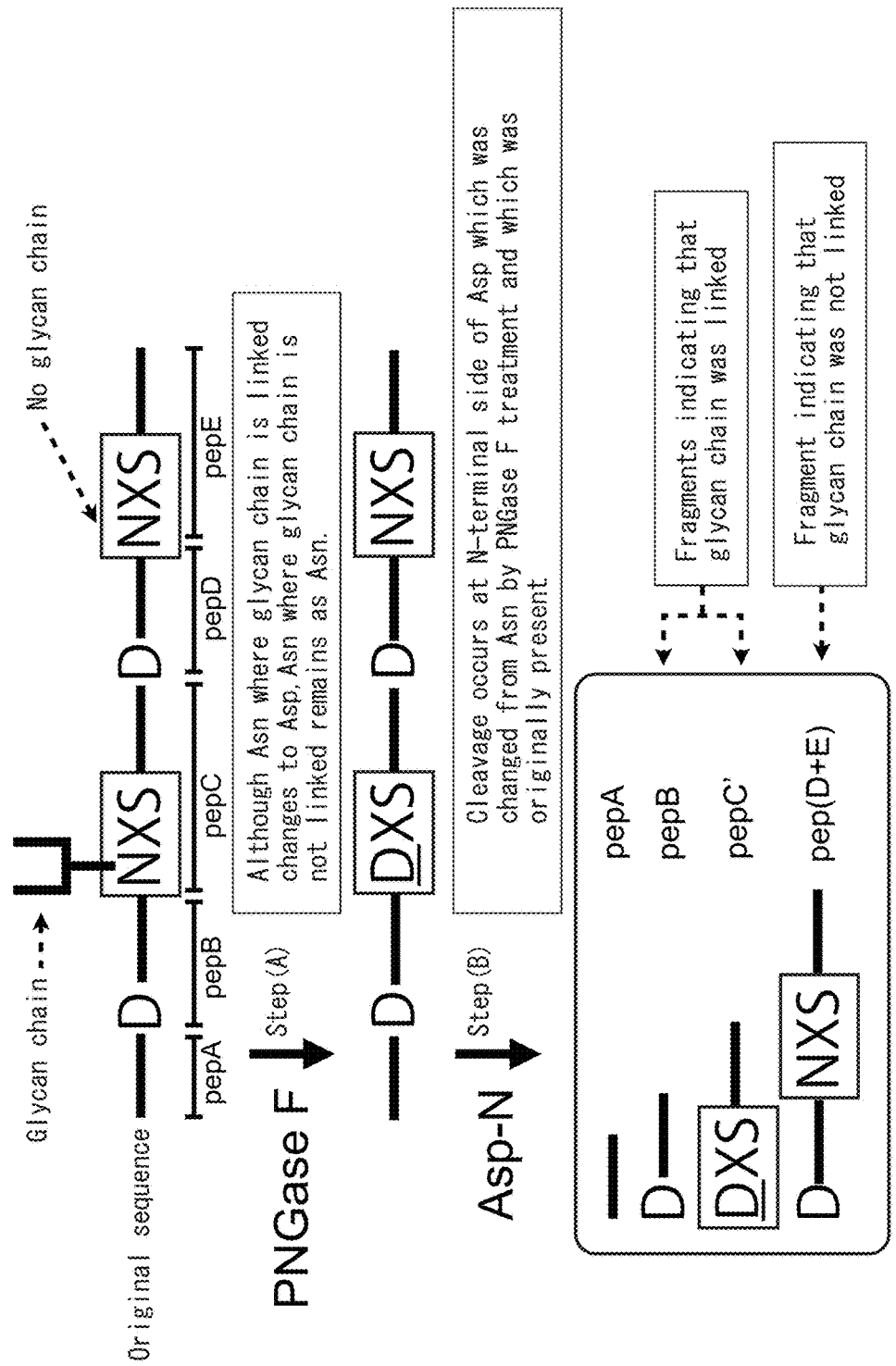
FIG. 1 is a drawing showing one example of the detection method of the present invention.
Figure 3:
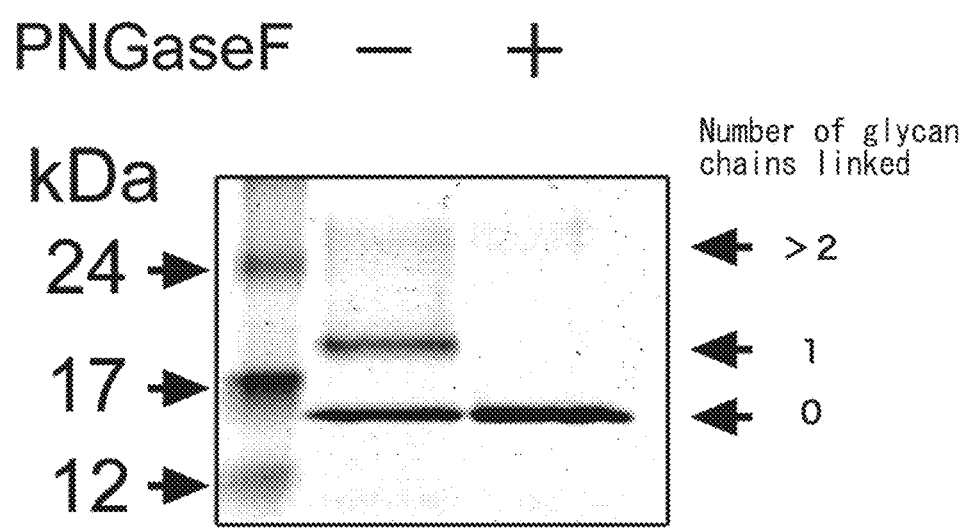
FIG. 3 is a drawing showing the results of separating human recombinant RNase 1 expressed by CHO cells by SDS-PAGE and the result of PNGase F treatment thereon.

The aforementioned recombinant human pancreas-specific RNase 1 was separated into a plurality of molecular weights by electrophoresis as indicated in the left lane (PNGase F(−)) of FIG. 3.

On the other hand, after reductively degenerating 20 µg of recombinant human pancreas-specific RNase 1, since the product of removing glycan chains by treating with PNGase F (New England Biolabs Inc.) resulted in a 15 kDa band that closely coincided with the molecular weight predicted from the amino acid sequence on electrophoresis (FIG. 3, right lane, PNGase F(+)), the aforementioned plurality of molecular weights was confirmed to be the result of differences in the numbers of glycan chains linked to the N-linked glycosylation sites.

Following separation by SDS-PAGE, the fragments were transferred to a PVDF membrane in accordance with ordinary methods. The transferred PVDF membrane was washed with ultrapure water followed by staining with a solution containing Coomassie Brilliant Blue R250, cutting out the portion corresponding to recombinant RNase 1 from which glycan chains had been removed, and subjecting to treatment for mass spectrometry. The cut out PVDF membrane was added to Tris buffer (pH 8.0) containing an endo-type peptidase in the form of Asp-N followed by treating for 20 hours at 37° C. The sample solution was then treated with ZipTip C18 (Millipore Corp.) and eluted into a matrix solution and spotted on a plate. After allowing to air dry, mass spectrometry was carried out according to the peptide mass fingerprint method using MALDI-TOFMS (Voyager-DE STR, Applied Biosystems, Inc.).

The left side of Table 1 shows peptide fragments formed during hydrolysis of the sequence of RNase 1 predicted from the gene sequence (SEQ ID NO. 2) with Asp-N and their theoretical masses. In addition, the right side of Table 1 shows peptide fragments formed during hydrolysis with Asp-N of a sequence in which all Asn residues at N-linked glycosylation sites, namely the Asn residues at positions 34, 76 and 88, changed to Asp residues (SEQ ID NO. 3) as a result of removing N-linked glycan chains by PNGase F from RNase 1, in which glycan chains were linked to all N-linked glycosylation sites, along with their theoretical masses. Theoretical mass indicates the value obtained by calculating the mass of those fragments in which all amino acid residues were not subjected to chemical modification. In addition, those peptide fragments that were able to be assigned as peptide fragments derived from RNase 1 by mass spectrometry were indicated with a O in the detection column while those that were unable to be assigned were indicated with an X.

TABLE 1

| Peptide fragments obtained by treating RNase 1 predicted from genetically encoded sequence with Asp-N and their theoretical masses | | | | Peptide fragments obtained by deglycosylating RNase 1 having glycan chains linked to all N-linked glycosylation sites with PNGase F and treating with Asp-N | | | |
|---|---|---|---|---|---|---|---|
| Amino Acid No. | Amino Acid Sequence | Theoretical Mass | Detection | Amino Acid No. | Amino Acid Sequence | Theoretical Mass | Detection |
| 1-13 | KESRAKKFQRQHM (SEQ ID NO. 4) | 1673.9016 | O | 1-13 | KESRAKKFQRQHM (SEQ ID NO. 4) | 1673.9016 | O |
| 14-15 | DS | 221.0768 | X | 14-15 | DS | 221.0768 | X |
| 16-52 | DSSPSSSSTYCNQMMRRRN MTQGRCKPVNTFVHEPLV (SEQ ID NO. 5) | 4243.9675 | X | 16-33 | DSSPSSSSTYCNQMMRRR (SEQ ID NO. 9) | 2092.8957 | O |
| | | | | 34-52 | DMTQGRCKPVNTFVHEPLV (SEQ ID NO. 10) | 2171.0736 | O |
| 53-82 | DVQNVCFQEKVTCKNGQGN CYKSNSSMHIT (SEQ ID NO. 6) | 3362.5021 | O | 53-75 | DVQNVCFQEKVTCKNGQGNCYKS (SEQ ID NO. 11) | 2592.1639 | O |
| | | | | 76-82 | DSSMHIT (SEQ ID NO. 12) | 790.3400 | X |

TABLE 1-continued

| | Peptide fragments obtained by treating RNase 1 predicted from genetically encoded sequence with Asp-N and their theoretical masses | | | | Peptide fragments obtained by deglycosylating RNase 1 having glycan chains linked to all N-linked glycosylation sites with PNGase F and treating with Asp-N | | |
|---|---|---|---|---|---|---|---|
| Amino Acid No. | Amino Acid Sequence | Theoretical Mass | Detection | Amino Acid No. | Amino Acid Sequence | Theoretical Mass | Detection |
| 83-120 | DCRLTNGSRYPNCAYRTSPKERHIIVACEGSPYVPVHF (SEQ ID NO. 7) | 4336.0960 | X | 83-87 | DCRLT (SEQ ID NO. 13) | 607.2868 | O |
| | | | | 88-120 | DGSRYPNCAYRTSPKEPHIIVACEGSPYVPVHF (SEQ ID NO. 14) | 3748.8111 | X |
| 121-125 | DASVE (SEQ ID NO. 8) | 520.2249 | X | 121-125 | DRSVE (SEQ ID NO. 8) | 520.2249 | X |
| 126-128 | DST | 322.1245 | X | 126-128 | DST | 322.1245 | X |

In the case of removing glycan chains with PNGase F, Asn residues where the glycan chains are linked are changed to Asp residues by the deamidase activity of PNGase F. Thus, a glycoprotein from which the glycan chains have been removed with PNGase F is subjected to hydrolysis by Asp-N on the N-terminal side of the amino acid residues where the glycan chains were originally linked. On the other hand, since Asn residues where glycan chains were not originally linked are not changed to Asp residues and remain as Asn residues, they are not subjected to hydrolysis by Asp-N. In this manner, the manner in which peptides at N-linked glycosylation sites are fragmented varies according to the presence or absence of the addition of glycan chains.

Table 2 shows the masses of peptide fragments described in Table 1 that were actually detected along with the amino acid sequences predicted when considering amino acid modification.

numbers were described for those peaks of the masses (m/z: 2663, 1499, 3433, 4771) of the peptide fragment adjacent to Asn76 (53-75) and the peptide fragment containing Asn76 (53-82).

Figure 5:
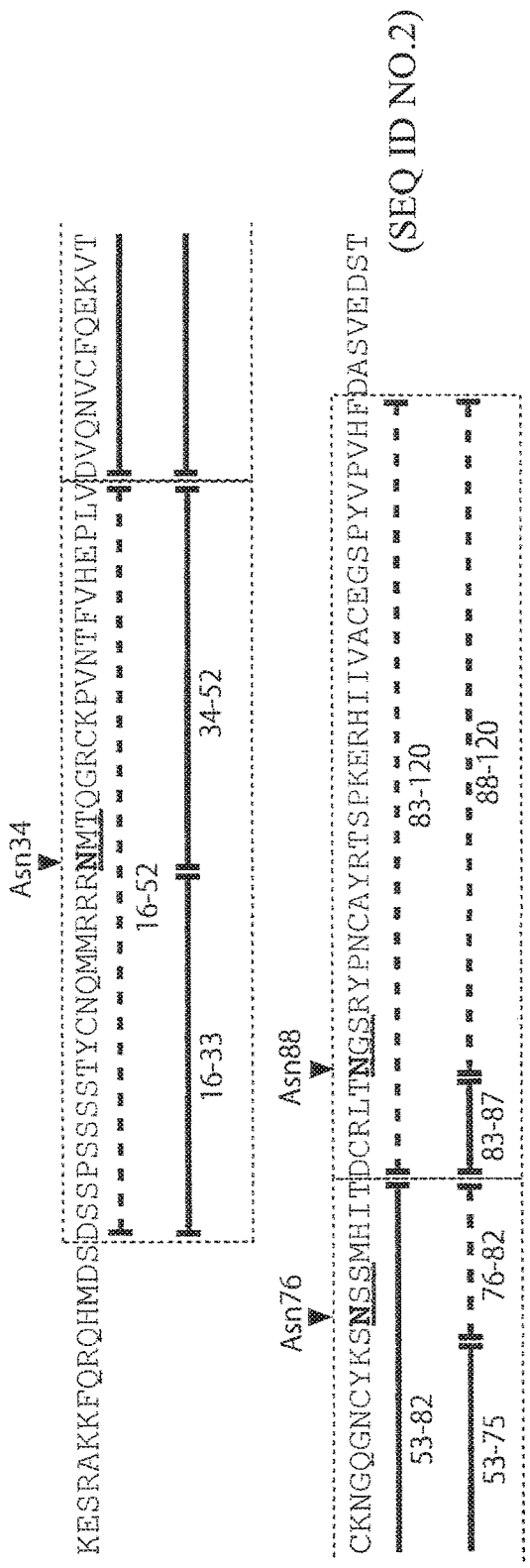
FIG. 5 is a drawing showing the presence or absence of detection of a fragment derived from an N-linked glycosylation site in the form of a peptide containing Asn34, Asn76 or Asn88 over the full-length sequence of RNase 1 in Example 1.

FIG. 5 shows those peptide fragments formed from RNase 1 that were detected and not detected in the peptide sequence of RNase 1 with respect to portions containing N-linked glycosylation sites. Solid lines indicate detected peptide fragments while broken lines indicate peptide fragments that were not detected, and their respective amino acid numbers are shown below the lines.

As shown in Table 1, in the fragment derived from the sequence containing Asn34, peptides were detected having masses corresponding to fragments 16-33 (DSSPSSSSTY-CNQMMRRR) (SEQ ID NO. 9) and 34-52 (DMTQGRCK-PVNTFVHEPLV) (SEQ ID NO. 10), indicating that an N-linked glycan chains were linked thereto, and no peptide

TABLE 2

| Amino Acid No. | Sequence | Detected Mass (mz) | Predicted Mass (mz) | Modified Amino Acid Residue: Type of Modification (Additional Mass) |
|---|---|---|---|---|
| 1-13 | KESPAKKFQRQHM (SEQ ID NO. 4) | 1673.8889 | 1672.8816 | None |
| | | 1689.8641 | 1688.8568 | Methionine: Oxidation (+16) |
| 16-33 | DSSPSSSSTYCNQMMRRR (SEQ ID NO. 9) | 2092.8999 | 2091.8927 | None |
| | | 2108.9119 | 2107.9049 | Methionine: Oxidation (+16) |
| | | 2163.9243 | 2162.9171 | Cysteine: Acrylamddation (+71) |
| | | 2179.9227 | 2178.9154 | Methionine: Oxidation (+16) Cysteine: Acrylamddation (+71) |
| | | 2196.0021 | 2194.9949 | Methionine: Oxidation x 2 (+32) Cysteine: Acrylamidation (+71) |
| 34-52 | DMTQGRCKPVNTFVHEPLV (SEQ ID NO. 10) | 2171.0681 | 2170.0680 | None |
| | | 2187.0475 | 2186.0402 | Methionine: Oxidation (+16) |
| | | 2242.1006 | 2241.0933 | Cysteine: AcrylAmidation (+71) |
| | | 2258.0760 | 2257.0687 | Methionine: Oxidation (+16) Cysteine: Acrylamddation (+71) |
| 53-75 | DVQNVCFQEKVTCKNGQGNCYKS (SEQ ID NO. 11) | 2663.1499 | 2662.1427 | Cystein: Acrylamidation (+71) |
| 53-82 | DVQNVCFQEKVTCKNGQGNCYKSNSSMHIT (SEQ ID NO. 6) | 3433.4771 | 3432.4699 | Cysteine: Acrylamidation (+71) |
| 83-87 | DCRLT (SEG ID NO. 13) | 607.3008 | 606.2936 | None |

Figure 4:
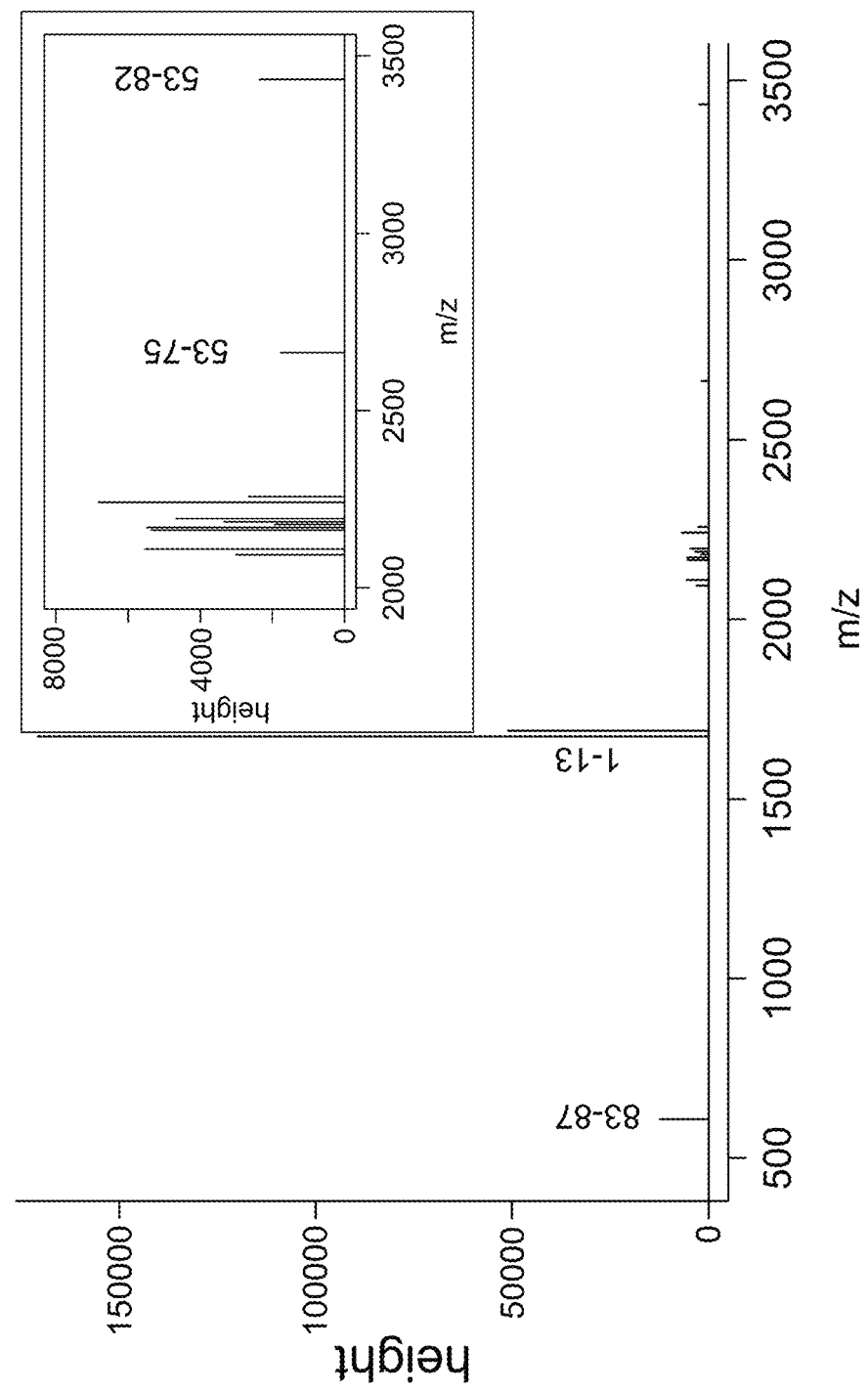
FIG. 4 is a drawing showing extraction of peptide fragments derived from RNase 1 in the mass spectrometry results of Example 1.

Mass spectrometry spectral data is shown in FIG. 4. A plurality of peptide sequences derived from RNase 1 was detected. In the drawing, the graph shown in the small frame is an enlarged view of the m/z range from 2000 to 3500, and among those peptides derived from RNase 1, amino acid indicating that no N-linked glycan chain was linked thereto was detected. In the fragment derived from the sequence containing Asn76, among those fragments indicating to have glycan chains linked thereto, the fragment 53-75 (DVQN-VCFQEKVTCKNGQGNCYKS) (SEQ ID NO. 11) was detected, but the fragment 76-82 (DSSMHIT) (SEQ ID NO. 12) was not detected. In addition, fragment 53-82 (DVQN-VCFQEKVTCKNGQGNCYKSNSSMHIT) (SEQ NO. 6), which was indicating that a glycan chain was not linked thereto, was also detected. In the fragment derived from the sequence containing Asn88, only the fragment 83-87 (DCRLT) (SEQ ID NO. 13) that was indicating to have a glycan chain linked thereto was detected, while the fragment 88-120 (DGSRYPNCAYRTSPKERHIIVACEG-SPYVPVHF) (SEQ ID NO. 14) was not detected. In addition, the fragment 83-120 (DCRLTNGSRYPNCAYRTSPK-ERHIIVACEGSPYVPVHF) (SEQ ID NO. 7), which was indicating not to have a glycan chain linked thereto, was not detected.

Among those fragments that were not detected, although the fragment containing Asn88 having amino acid Nos. 88-120 was present since fragment 83-87, to which a pair of glycan chains were linked, was detected, since it is a molecule having a comparatively large molecular size, it is thought to not have been detected due to limitations on the measuring instrument. In the case of this fragment, since the theoretical mass when not taking into consideration amino acid modification is 3748.8111, a fragment having a mass larger than this is thought to not be detected due to limitations on the measuring instrument. Accordingly, although peptide fragments corresponding to amino acid Nos. 16-52 (theoretical mass: 4243.9675) and amino acid nos. 83-120 (theoretical mass: 4336.0960) were not detected, since these are molecules having larger theoretical masses, whether or not they were initially not present or were unable to be detected despite being present due to limitations on the measuring instrument was unable to be confirmed. Furthermore, amino acid Nos. 76-82 are located in a region of high background noise and were not detected.

In this manner, in the case of Asn34, Asn76 and Asn88, molecules were clearly present to which glycan chains were respectively linked. In addition, with respect to those molecules to which glycan chains were not linked, although a molecule to which a glycan chain was not linked was clearly present in Asn76, this was unable to be confirmed with respect to Asn34 and Asn88.

Figure 6:
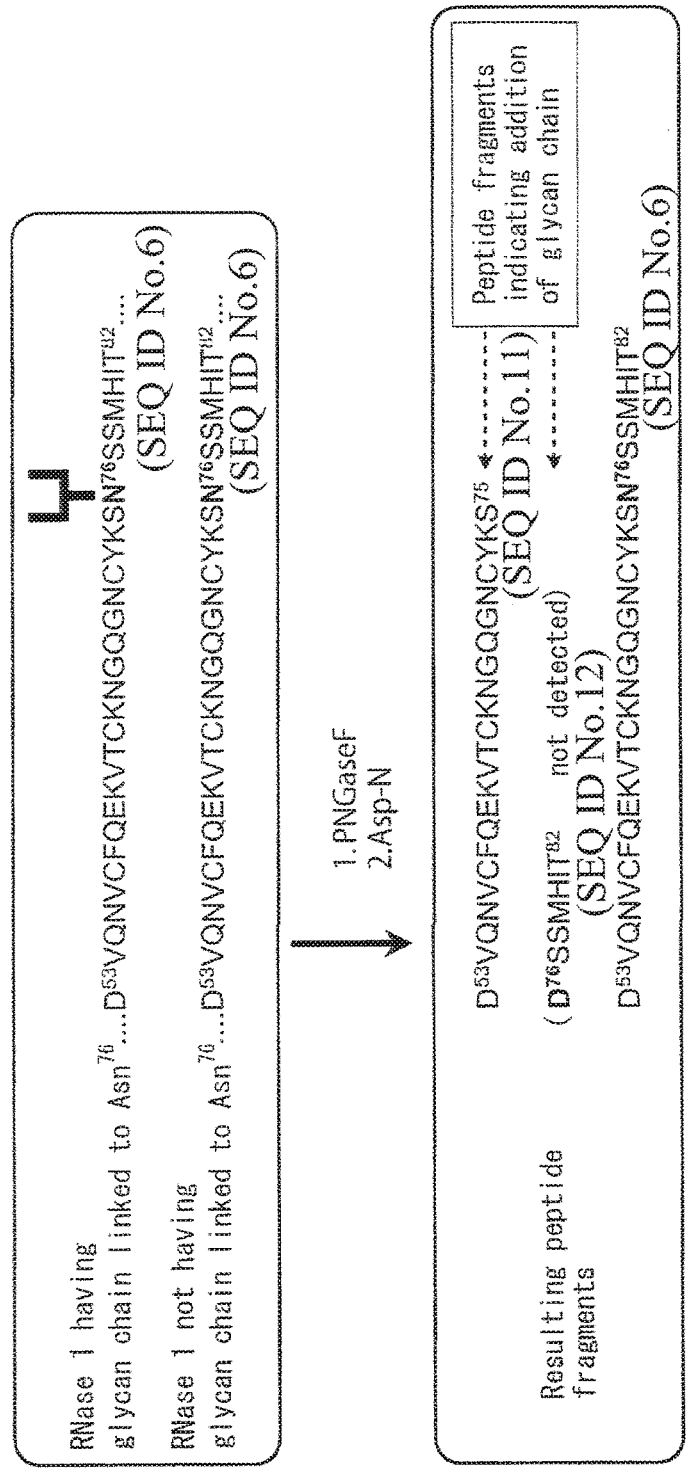
FIG. 6 is a drawing schematically representing the relationship between the presence or absence of glycosylation at a glycosylation site and the detected peptide in Example 1.

In addition, as shown in FIG. 3, although the recombinant RNase 1 expressed in CHO cells was suggested to have a plurality of types of molecular species having different states of glycan chain addition, according to the aforementioned analysis method, a portion of those glycan chain addition states was clearly determined. Namely, since two types of peptide fragments having different masses were detected that were derived from the sequence of RNase 1 containing Asn76, as shown in FIG. 6, in the case of Asn76 at N-linked glycosylation sites, a mixed state was able to be confirmed by mass spectrometry that consisted of a peptide fragment having a glycan chain linked thereto and a glycan chain not having a glycan chain linked thereto.

Example 2

Determination of N-Linked Glycosylated Sites of RNase 1 Treated with Asp-N and Lys-C RNase 1 expressed in CHO cells used in Example 1 was carbamidomethylated in accordance with ordinary methods to obtain an analysis sample (carbamidomethylated RNase 1), and the analysis sample was fragmented into peptides with endo-type peptidases Asp-N and Lys-C, and then analyzed with a mass spectrometer. The following provides a description of the analysis procedure. After deglycosylating the carbamidomethylated RNase 1 with PNGase F in the same manner as Example 1, the fragments were separated by SDS-PAGE and transferred to a PVDF membrane in accordance with ordinary methods. After washing the transferred PVDF membrane with ultrapure water, the membrane was stained with a solution containing Coomassie Brilliant Blue R250, and the portion corresponding to the recombinant RNase 1 that had been removed of glycan chains was cut out and subjected to treatment for mass spectrometry. The cut out PVDF membrane was added to Tris buffer (pH 8.0) containing the endo-type peptidase Lys-C, and after treating for 20 hours at 37° C., the endo-type peptidase Asp-N was added followed by further treating for 20 hours at 37° C. The sample solution was treated with ZipTip C18 (Millipore Corp.) and eluted into a matrix solution and spotted on a plate. After allowing to air dry, mass spectrometry was carried out according to the peptide mass fingerprint method using MALDI-TOFMS (AXIMA-Confidence, Shimadzu Corp., measuring range: m/z 800-4000).

The left side of Table 3 shows peptide fragments formed during hydrolysis of the sequence of RNase 1 predicted from the gene sequence with Asp-N and Lys-C and their theoretical masses, while the right side shows peptide fragments formed during hydrolysis with Asp-N and Lys-C after removing glycan chains with PNGase F from RNase 1 in the case of N-linked glycan chains linked to all N-linked glycosylation sites, along with their theoretical masses. Theoretical mass indicates the value obtained by calculating the mass of those fragments in which all amino acid residues were not subjected to chemical modification. Those peptide fragments that were able to be assigned as peptide fragments derived from RNase 1 by mass spectrometry were indicated with a O in the detection column while those that were unable to be assigned were indicated with an X.

TABLE 3

| Peptide fragments obtained by treating RNase 1 predicted from genetically encoded sequence with Asp-N/Lys-C and their theoretical masses | | | | Peptide fragments obtained by deglycosylating RNase 1 having glycan chains linked to all N-linked glycosylation sites with PNGase F and treating with Asp-N/Lys-C | | | |
|---|---|---|---|---|---|---|---|
| Amino Acid No. | Amino Acid Sequence | Theoretical Mass | Detection | Amino Acid No. | Amino Acid Sequence | Theoretical Mass | Detection |
| 1 | K | 147.1128 | X | 1 | K | 147.1128 | X |
| 2-6 | ESRAK (SEQ ID NO. 15) | 590.3256 | X | 2-6 | ESRAK (SEQ ID NO. 15) | 590.3256 | X |

TABLE 3-continued

| | Peptide fragments obtained by treating RNase 1 predicted from genetically encoded sequence with Asp-N/Lys-C and their theoretical masses | | | | Peptide fragments obtained by deglycosylating RNase 1 having glycan chains linked to all N-linked glycosylation sites with PNGase F and treating with Asp-N/Lys-C | | |
|---|---|---|---|---|---|---|---|
| Amino Acid No. | Amino Acid Sequence | Theoretical Mass | Detection | Amino Acid No. | Amino Acid Sequence | Theoretical Mass | Detection |
| 7 | K | 147.1128 | X | 7 | K | 147.1128 | X |
| 8-13 | FQRQHM (SEQ ID NO. 16) | 846.4039 | O | 3-13 | FQRQHM (SEQ ID NO. 16) | 846.4039 | O |
| 14-15 | DS | 221.0768 | X | 14-15 | DS | 221.0768 | X |
| 16-52 | DSSPSSSSTYCNQMMRPRNMTQGRCKPVNTFYEEPLV (SEQ ID NO. 5) | 4243.9675 | X | 16-33 | DSSPSSSSTYCNQMNRRP (SEQ ID NO. 9) | 2092.8957 | O |
| | | | | 34-52 | DMTQGRCKPVNTFVHEPLV (SEQ ID NO. 10) | 2171.0736 | O |
| 53-62 | DVQNVCFQEK (SEQ ID NO. 17) | 1209.5568 | O | 53-62 | DVQNVCFQEK (SEQ ID NO. 17) | 1209.5568 | O |
| 63-66 | VTCK (SEQ ID NO. 18) | 450.2381 | X | 63-66 | VTCK (SEQ ID NO. 18) | 450.2381 | X |
| 67-74 | NGQGNCYK (SEQ ID NO. 19) | 883.3727 | X | 67-74 | NGQGNCYK (SEQ ID NO. 19) | 883.372 | X |
| 75-82 | SNSSMHIT (SEQ ID NO. 20) | 876.3880 | X | 75 | S | | X |
| | | | | 76-82 | DSSMHIT (SEQ ID NO. 12) | 790.3400 | X |
| 83-102 | DCRLTNGSRYPNCAYRTSPK (SEQ ID NO. 21) | 2302.0815 | O | 83-87 | DCRLT (SEQ ID NO. 13) | 607.2868 | O |
| | | | | 88-102 | DGSRYPNCAYRTSPK (SEQ ID NO. 23) | 1714.7966 | O |
| 103-120 | ERHIIVACEGSPYVPVHF (SEQ ID NO. 22) | 2110.0538 | O | 103-120 | ERHIIVACEGSPYVPVHF (SEQ ID NO. 22) | 2110.0538 | O |
| 121-125 | DASVE (SEQ ID NO. 8) | 520.2249 | X | 121-125 | DASVE (SEQ ID NO. 8) | 520.2249 | X |
| 126-128 | DST | 322.1245 | X | 126-128 | DST | 322.1245 | X |

Table 4 shows the masses of peptide fragments that were actually detected along with the amino acid sequences predicted when considering amino acid modification.

TABLE 4

| Amino Acid No. | Sequence | Detected Mass (m/z) | Predicted Mass (m/z) | Modified Amino Acid Residue: Type of Modification (Additional Mass) |
|---|---|---|---|---|
| 2-15 | ESRAKKFQRQHMDS (SEQ ID NO. 27) | 1747.8600 | 1746.8527 | None |
| 7-13 | KFQRQHM (SEQ ID NO. 24) | 974.4300 | 973.4227 | None |
| 7-15 | KFQRQHMDS (SEQ ID NO. 25) | 1192.5500 | 1191.5427 | Methionine: Oxidation (+16) |
| 8-13 | FQRQHM (SEQ ID NO. 16) | 846.4100 | 845.4027 | None |
| 16-33 | DSSPSSSSTYCNQMMRRR (SEQ ID NO. 9) | 2093.0800 | 2092.0727 | None |
| | | 2109.0600 | 2108.0527 | Methiondne: Oxidation (+16) |
| 34-52 | DMTQGRCKPVNTFVHEPLV (SEQ ID NO. 10) | 2171.1600 | 2170.1527 | None |
| | | 2187.2000 | 2186.1927 | Methionine: Oxidation (+16) |
| 53-62 | DVQNVCFQEK (SEQ ID NO. 17) | 1209.5300 | 1208.5227 | None |
| | | 1266.6800 | 1265.6727 | Cysteine: Carbamidomethylation (+57) |
| 67-82 | NGQGNCYKSNSSMHIT (SEQ ID NO. 26) | 1813.8700 | 1812.8627 | Cysteine: Carbamidomethylatdon (+57) Methionine: Oxidation (+16) |

TABLE 4-continued

| Amino Acid No. | Sequence | Detected Mass (m/z) | Predicted Mass (m/z) | Modified Amino Acid Residue: Type of Modification (Additional Mass) |
|---|---|---|---|---|
| 83-102 | DCRLTNGSRYPNCAYRTSPK (SEQ ID NO. 21) | 2301.2800 2416.3600 | 2302.0815 2415.3527 | None Cysteine: Carbamidomethylation × 2 (+114) |
| 88-102 | DGSRYPNCAYRTSPK (SEQ ID NO. 23) | 1714.8600 1771.8900 | 1713.8527 1770.8827 | None Cysteine: Carbamidomethylation: (+57) |
| 103-120 | ERHIIVACEGSPYVPVHF (SEQ ID NO. 22) | 2053.1400 2110.1900 | 2052.0251 2109.1827 | None Cysteine: Carbamidomethylation (+57) |

Furthermore, although amino acid nos. 2-15 (SEQ ID NO. 27), 7-13 (SEQ ID NO. 24), 7-15 (SEQ ID NO. 25) and 67-82 (SEQ ID NO. 26) are peptide fragments not described in Table 3, these are presumed to have been formed due to hydrolysis by Asp-N and Lys-C not proceeding completely.

As described in Example 1, in the case of having removed glycan chains with PNGase F, Asn residues having a glycan chain linked thereto changed to Asp residues due to the deamidase activity of PNGase F. Thus, in a glycoprotein in which glycan chains have been removed with PNGase F, Asn residues originally having glycan chains linked thereto are changed to Asp residues, and the N-terminal sides thereof are subjected to decomposition by Asp-N. On the other hand, since Asn residues originally not having a glycan chain linked thereto do not change to Asp residues, they are not subjected to hydrolysis by Asp-N. In addition, since Lys-C is an enzyme that hydrolyzes peptide bonds on the C-terminal side of a lysine group, with the exception of the case in which a proline residue is linked to the C-terminal side, they are not involved in peptide fragmentation around glycosylation sites. Accordingly, in the case of using Lys-C in addition to Asp-N, the manner in which fragments containing N-linked glycosylation sites are fragmented varies according to the presence or absence of the addition of glycan chains. Moreover, since treatment with both Asp-N and Lys-C is expected to result in shorter detected peptide fragments than treatment with Asp-N alone, fragments that were unable to be detected due to limitations on the performance of the measuring instrument as in Example 1 are thought to be able to be determined.

Figure 7:
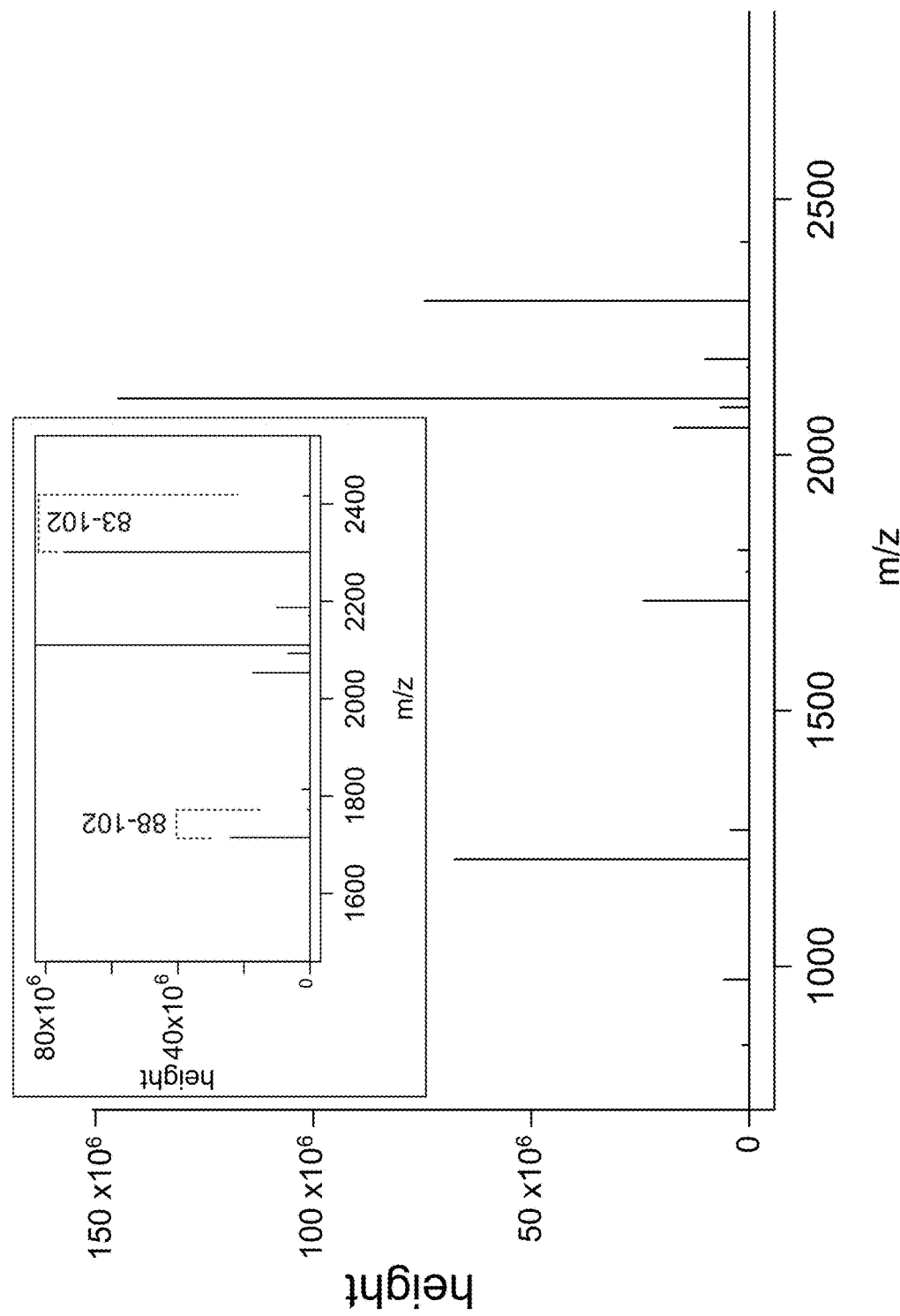
FIG. 7 is a drawing showing extraction of peptide fragments derived from RNase 1 in the mass spectrometry results of Example 2.

Mass spectrometry spectral data is shown in FIG. 7. A plurality of peptides derived from RNase 1 were detected. In the drawing, the graph shown in the small frame is an enlarged view of the m/z range from. 1500 to 2500, and among those peptides derived from RNase 1, amino acid numbers were described for those peaks of the mass of peptide fragment 88-102 containing Asn88 (m/z: 1714.8600, 1771.8900) and the mass of peptide fragment 83-102 (m/z: 2301.2800, 2416.3600).

As is clear from Table 3, Asn34 and Asn88 were clearly determined to each have molecules where glycan chains are linked. In addition, with respect to Asn76, a fragment shown to have a glycan chain linked thereto in the form of amino acid Nos. 76-82 (SEQ ID NO. 12) was in an area of high background noise and was unable to be detected. On the other hand, with respect to molecules to which glycan chains are not linked, since the fragment containing Asn34 (amino acid Nos. 16-52) has a large theoretical mass (4243.9675) that is beyond the determination limit of the mass spectrometer (4000), whether it was unable to be detected despite being present due to limitations on the measuring instrument or was initially not present was unable to be confirmed. With respect to Asn76, since a fragment corresponding to amino acid Nos. 67-82, which was predicted to have been formed as a result of hydrolysis by endo-type peptidase Lys-C not proceeding completely, was detected as shown in Table 4, a molecule to which a glycan chain is not linked was clearly determined to be present. In addition, since amino acid Nos. 83-102 were detected as a fragment containing Asn88, a molecule to which a glycan chain is not linked was clearly determined to be present in Asn88.

Figure 8:
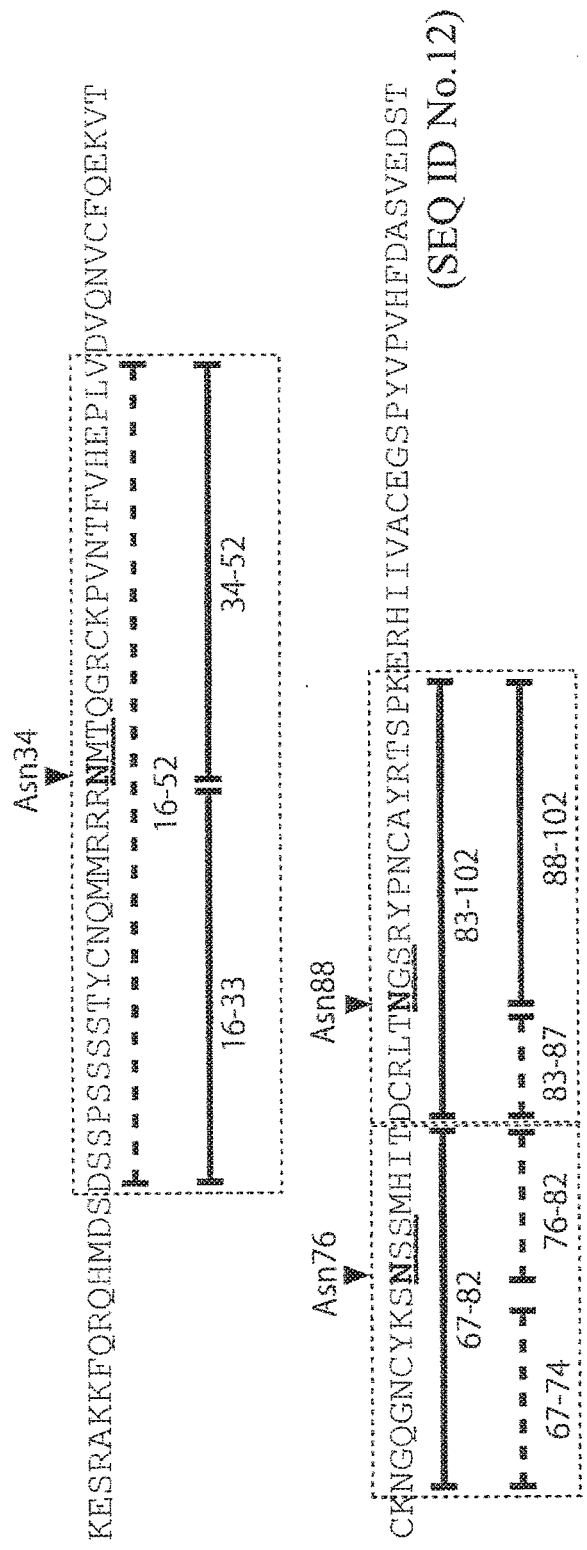
FIG. 8 is a drawing showing the presence or absence of detection of a fragment derived from an N-linked glycosylation site in the form of a peptide containing Asn34, Asn76 or Asn88 over the full-length sequence of RNase 1 in Example 2.
Figure 9:
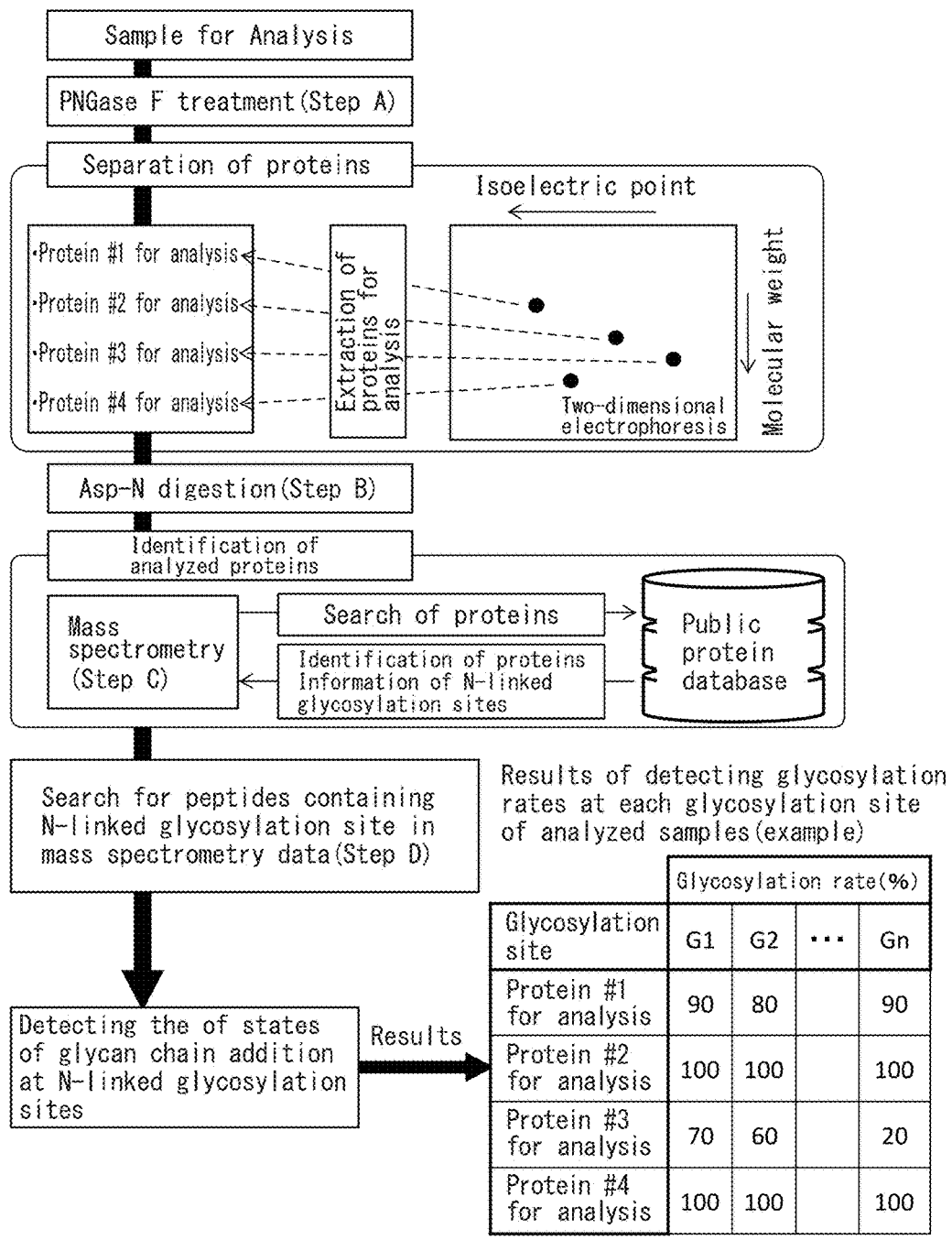
FIG. 9 is a drawing showing one example of an embodiment of the present invention.

In addition, FIG. 8 shows those peptide fragments formed from RNase 1 that were detected and not detected with respect to portions containing N-linked glycosylation sites in the peptide sequence of RNase 1. Solid lines indicate detected peptide fragments while broken lines indicate peptide fragments that were not detected, and their respective amino acid numbers are shown below the lines.

In the case of Example 1, the peptide fragment of amino acid Nos. 83-120 formed in the case a glycan chain is not linked to Asn88 of RNase 1 (DCRLTNGSRYPNCAYRTSP-KERHIIVACEGSPYVPVHF) (SEQ ID NO. 7) and a peptide fragment from amino acid Nos. 88-120 among peptide fragments in the case a glycan chain is linked to Asn88 (DGSRYPNCAYRTSPKERHIIVACEGSPYVPVHF) (SEQ ID NO. 14) were unable to be detected. In contrast, since the molecular weights of peptide fragments obtained by digesting with Asn-N and Lys-C were lower, a peptide fragment of amino acid Nos. 83-102 formed in the case a glycan chain is not linked to Asn88 of RNase 1 (DCRLTNGSRYPNCAYRTSPK) (SEQ ID NO. 21) and a peptide fragment of amino acid Nos. 88-102 formed in the case a glycan chain is linked to Asn88 (DGSRYPNCAYRTSPK) (SEQ ID NO. 23) were able to be detected in Example 2. In Example 2, since two types of peptide fragments consisting of peptide fragments containing an asparagine residue at position 88, or an Asp residue to which it had changed, were detected at amino acid Nos. 83-102 and amino acid residues 88-102, the recombinant RNase 1 expressed in CHO cells used as a sample was confirmed to consist of a mixture of RNase 1 in a state in which a glycan chain is linked to Asn88 and a state in which a glycan chain is not linked.

In this manner, the use of not only an enzyme that recognizes Asp residues, but also a different endo-type peptidase that does not recognize Asp residues or Asn residues, makes it possible to detect peptide fragments more precisely.

Based on the results of Examples 1 and 2, recombinant RNase 1 expressed in CHO cells was clearly determined to consist of mixture of N-linked glycan chain addition states at Asn76 and Asn88.

Example 3

Analysis of Glycan Chain Addition State of Human Interferon Gamma

Human interferon gamma (SEQ ID NO. 28), which is used in pharmaceuticals in the form of antivirus drugs or anticancer agents, has two N-linked glycosylation sites as predicted from its amino acid sequence (Asn25, Asn97).

Commercially available research reagents in the form of recombinant human interferon gamma expressed in an *Escherichia coli* expression system (Peprotech Inc., Cat. No. 300-02) and recombinant human interferon gamma expressed in a. CHO cell expression system (Sino Biological Inc., Cat. No. 11725-HNAS) were respectively acquired and analyzed for the presence or absence of glycosylation at the N-linked glycosylation sites as unglycosylated recombinant human interferon gamma expressed in *Escherichia coli* and glycosylated recombinant human interferon gamma expressed in CHO cells.

Results of LC-MS/MS Analysis of Recombinant Human interferon Gamma Expressed in *Escherichia coli*

Figure 10:
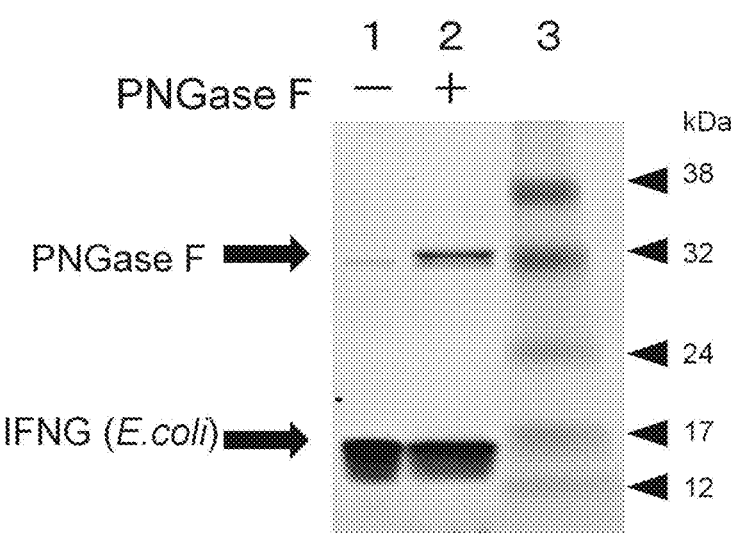
FIG. 10 is a drawing showing the results of separating human interferon gamma expressed in *Escherichia coli* by SDS-PAGE and the result of PNGase F treatment thereon in Example 3.

The results of separating 2 µg of recombinant human interferon gamma expressed in *Escherichia coli* by SDS-PAGE electrophoresis in accordance with ordinary methods followed by CBB staining are shown in FIG. 10. Since the recombinant protein is not subjected to glycosylation in the *Escherichia coli* expression system, a single band was detected at about 16 Da (Lane 1). Even if this sample was treated with PNGase F, a band was obtained at the same location as that of the protein prior to treatment (Lane 2).

On the other hand, 20 µg of recombinant human interferon gamma expressed in *Escherichia coli* were separated by SOS-PAGE and then transferred to a PVDF membrane in accordance with ordinary methods. The transferred PVDF membrane was washed with ultrapure water and then stained with a solution containing Coomassie Brilliant Blue R250, after which the 16 kDa band corresponding to the recombinant human interferon gamma expressed in *Escherichia coli* was cut out and used as a sample for mass spectrometry. The cut out PVDF membrane was added to Tris buffer (pH 8.0) containing the endo-type peptidase Asp-N and treated for 20 hours at 37° C. After separating the sample solution with an HPLC system (Advance UHPLC System, Michrom Bioresources, Inc.), analysis was carried out using a mass spectrometer connected thereto (Thermo Scientific LTQ Orbitrap XL Mass Spectrometer, Thermo Fisher Scientific Inc.).

Peptides having masses of 1963.01 Da, 1618.80 Da, 1503.78 Da and 1430.66 Da were detected in LC-MS/MS analysis (Table 5). Moreover, when the internal sequences were determined for each of these peaks by tandem MS, peptides exhibiting each of these masses were confirmed to be peptides corresponding to amino acid nos. 24-40, 62-75, 63-75 and 90-101 of the sequence shown in SEQ ID NO. 28.

TABLE 5

Results of LC-MS/MS Analysis of Recombinant Human Interferon Gamma Expressed in *Escherichia coli* (Absence of PNGase Treatment)

| Detected Peptide Mass (Da) | m/z | Ionic Valence | Sequence Range |
|---|---|---|---|
| 1963.01 | 982.51 | 2 | 24-40 |
|  | 655.34 | 3 | 24-40 |
| 1618.80 | 810.41 | 2 | 62-75 |
|  | 540.61 | 3 | 62-75 |
| 1503.78 | 752.90 | 2 | 63-73 |
|  | 502.27 | 3 | 63-73 |
| 1430.66 | 716.34 | 2 | 90-101 |

Next, a sample obtained by treating 20 µg of recombinant human interferon gamma expressed in *Escherichia coli* with PNGase F was treated with the endo-type peptidase Asp-N using the same method as explained above and then analyzed by LC-MS/MS (Table 6).

TABLE 6

Results of LC-MS/MS Analysis of Recombinant Human Interferon Gamma Expressed in *Escherichia coli* (Presence of PNGase Treatment)

| Detected Peptide Mass (Da) | m/z | Ionic Valence | Sequence Range |
|---|---|---|---|
| 2209.08 | 1105.55 | 2 | 2-20 |
|  | 737.37 | 3 | 2-20 |
| 1963.01 | 982.51 | 2 | 24-40 |
|  | 655.34 | 3 | 24-40 |
| 1618.80 | 810.41 | 2 | 62-75 |
|  | 540.61 | 3 | 62-75 |
| 1503.78 | 752.90 | 2 | 63-75 |
|  | 502.27 | 3 | 63-75 |
| 1770.92 | 886.47 | 2 | 76-89 |
|  | 591.31 | 3 | 76-89 |
| 1430.66 | 716.34 | 2 | 90-101 |
| 1315.63 | 658.82 | 2 | 91-101 |

As is clear from Tables 5 and 6, peptide fragments detected in Table 5 (Results of LC-MS/MS Analysis of Recombinant Human Interferon Gamma Expressed in *Escherichia coli* (Absence of PNGase Treatment)) were also detected in Table 6. In particular, the results of Tables 5 and 6 completely coincided with respect to peptides corresponding to amino acid Nos. 24-40 and 90-101 of SEQ ID NO. 28, which are peptide fragments containing N-linked glycosylation sites. Accordingly, the recombinant human interferon gamma expressed in *Escherichia coli* can be judged to not have a glycan chain linked to the N-linked glycosylation site. This result agrees with the fact that glycan chains are not linked to recombinants expressed in *Escherichia coli*. In addition, this result indicates that Asn not having a glycan chain linked thereto is not converted to Asp during the course of treatment with PNGase F, and even in the case of having treated a glycoprotein that is partially subjected to N-linked glycosylation with PNGase F, Asn residues at N-linked glycosylation sites where a glycan chain is not linked are not converted to Asp residues, thereby indicating that Asn having an N-linked glycan chain linked thereto can be distinguished from Asn not having an N-linked glycan chain linked thereto by using the series of methods presented in the present invention.

Figure 11:
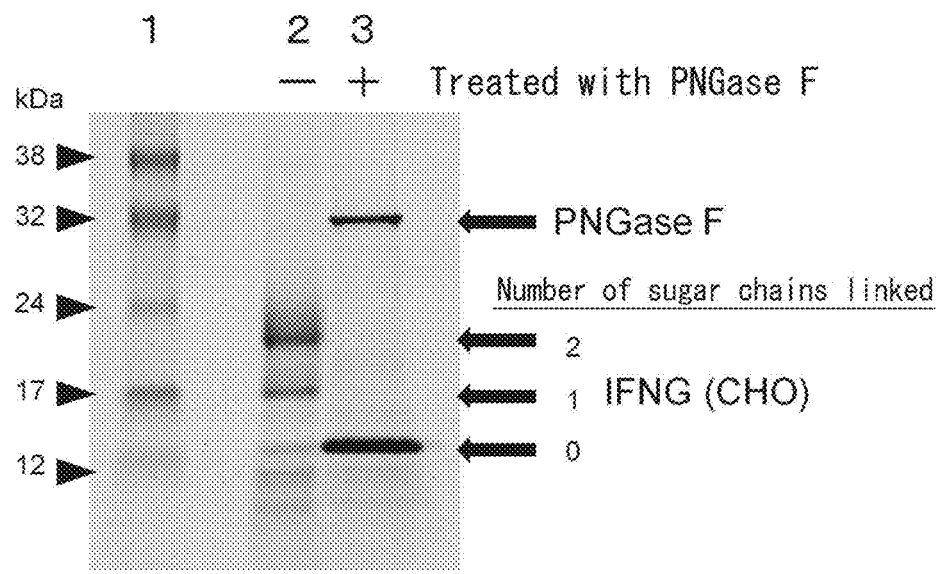
FIG. 11 is a drawing showing the results of separating human interferon gamma expressed in mammalian CHO-K1 cells by SDS-PAGE and the result of PNGase F treatment thereon in Example 3.

Results of LC/MS-MS Analysis of Recombinant Human Interferon Gamma Expressed in CHO Cells Since recombinant human interferon gamma obtained in a CHO cell expression system is subjected to N-linked glycosylation, in the case of not subjecting to deglycosylation treatment with PNGase F, a plurality of bands of about 14 kDa, about 17 kDa and about 20 kDa were detected in which molecular weights had shifted to higher molecular weights by an amount equal to the mass of the N-linked glycan chains on SDS-PAGE (FIG. 11). When this sample was treated with PNGase F, since the bands at about 17 kDa and about 20 kDa disappeared and converged into the band at about 14 kDa, the band at about 17 kDa was thought to represent two glycosylation sites, with a glycan chain linked to one of the sites, and the band at about 20 kDa was thought to represent two glycosylation sites, with a glycan chain linked to two of the sites. Namely, the analyzed sample was confirmed to be in a mixed state in which glycan chains were not linked to a portion of the glycosylation sites.

10 µg of recombinant human interferon gamma expressed in CHO cells and treated with PNGase F were separated by SDS-PAGE and then transferred to a PVDF membrane in accordance with ordinary methods. The transferred PVDF membrane was washed in ultrapure water and then stained with a solution containing Coomassie Brilliant Blue R250, after which a 14 kDa band corresponding to recombinant human interferon gamma from which glycan chains had been removed was cut out and subjected to treatment for mass spectrometry. The cut out PVDF membrane was added to Tris buffer (pH 8.0) containing the endo-type peptidase Asp-N and treated for 20 hours at 37° C., after which the resulting sample was analyzed by LC-MS/MS. The sample solution was separated with an HPLC system (Advance UHPLC System, Michrom Bioresources, Inc.) connected to a mass spectrometer (Thermo Scientific LTQ Orbitrap XL Mass Spectrometer, Thermo Fisher Scientific Inc.).

Peptides having masses of 1963.99 Da, 1618.81 Da, 1503.78 Da, 1770.92 Da, 866.40 Da, 1430.66 Da and 1315.63 Da were detected in LC-MS/MS analysis (Table 7). Moreover, when the internal amino acid sequences were determined for each of the detected peptide fragments having respective masses by tandem MS, peptides indicating each mass were confirmed to be peptides corresponding to amino acid Nos. 24-40, 62-75, 63-75, 76-89, 90-96, 90-101 and 91-101 shown in SEQ ID NO. 28. Since peptide fragments corresponding to amino acid Nos. 62-75, 63-75 and 76-89 in SEQ ID NO. 28 do not have internal N-linked glycosylation sites, these fragments are not subjected to changes in the amino acid sequence as a result of going through step (A). Since the amino acid sequence of this fragment coincides with the previously reported amino acid sequence of human interferon gamma, the analyzed sample was confirmed to be human interferon gamma. A fragment of 1963.99 Da was detected for a peptide containing an N-linked glycosylation site (Asn25). This peptide fragment was confirmed to consist of DDGTLFLGILKNWKEES (SEQ ID NO. 29) by tandem mass spectrometry. The sequence on the side of the N-terminal of this peptide was the sequence AspAsp, and the second Asp is an amino acid derived from the N-linked glycosylation site (Asn25). This peptide fragment (SEQ ID NO. 29) differs from a peptide fragment obtained by similarly hydrolyzing human interferon gamma not having a glycan chain, and since it contains an N-linked glycosylation (position 25), a glycan chain can be judged to be linked to Asp25 serving as the N-linked glycosylation site.

Furthermore, in the case a glycan chain is linked to Asn of a sequence consisting of AsnAsn as in the present example, although a phenomenon is observed in which the peptide cannot be completely digested in step (B) even if using Asp-N, it is still possible to judge the presence or absence of the addition of a glycan chain. In the case this phenomenon is observed, the peptide can be completely digested by using endoproteinase Glu-C, which is known to recognize an Asp moiety and decompose the peptide on the C-terminal side thereof in phosphate buffer (pH 7.8).

On the other hand, three fragments of 866.40 Da, 1430.66 Da and 1315.63 Da were detected for the peptide containing an N-linked glycosylation site (Asn97) or peptide adjacent thereto. Although an 866.40 Da peptide fragment was detected corresponding to amino acid nos. 90-96 of SEQ ID NO. 28, since this peptide fragment differed from the peptide fragment obtained by similarly hydrolyzing human interferon gamma not having a glycan chain with Asp-N, and did not contain an amino acid residue adjacent to the N-linked glycosylation site (position 97), an N-linked glycan chain can be judged to be linked to the Asn residue at position 97 of SEQ ID NO. 28. On the other hand, although peptide fragments having masses of 1430.66 Da and 1315.63 Da corresponding to amino acid nos. 90-101 and 91-101 of SEQ ID NO. 28 were detected, since these were the same peptides as the peptide fragment obtained by similarly hydrolyzing human interferon gamma not having a glycan chain, and contained an N-linked glycosylation site (position 97), an N-linked glycan chain can be judged to not be linked to the Asn residue at position 97 of SEQ ID NO. 28. On the basis of these two results, both an Asn residue where a glycan chain is linked and an Asn residue where a glycan chain is not linked can be confirmed to exist for the Asn residue at position 97 of recombinant human interferon gamma expressed in CHO cells. This coincided with the sample not subjected to deglycosylation treatment by PNGase F (Lane 2) that indicated bands corresponding to a plurality of molecular weights in FIG. 11.

TABLE 7

Results of LC-MS/MS Analysis of Recombinant Human Interferon Gamma Expressed in CHO Cells

| Detected Peptide Mass (Pa) | m/z | Ionic Valence | Sequence Range |
| --- | --- | --- | --- |
| 1963.99 | 983.00 | 2 | 24-40 (Asn25→Asp25) |
|  | 655.67 | 3 | 24-40 (Asn25→Asp25) |
| 1618.81 | 810.41 | 2 | 62-75 |
|  | 540.61 | 3 | 62-75 |
| 1503.78 | 752.90 | 2 | 63-75 |
|  | 502.27 | 3 | 63-75 |
| 1770.92 | 591.31 | 3 | 76-89 (Met77, oxidation) |
| 866.40 | 434.21 | 2 | 90-96 |
| 1430.66 | 716.8381 | 2 | 90-101 |
| 1315.63 | 658.82 | 2 | 91-101 |

The invention claimed is:

1. A method for detecting a site where an N-linked glycan chain is linked and/or a site where an N-linked glycan chain is not linked in a glycoprotein, comprising:

(A) removing an N-linked glycan chain from an N-linked glycosylated glycoprotein and changing an asparagine residue to which the N-linked glycan chain is linked to an aspartic acid residue;

(B) hydrolyzing the glycoprotein obtained in step (A) specifically for the asparagine residue or aspartic acid residue to obtain peptide fragments;

(C) detecting the peptide fragments obtained in step (B); and (D) by comparing with a peptide fragment obtained by hydrolyzing in the same manner as step (B) a protein having the same amino acid sequence as the original N-linked glycosylated glycoprotein but not having a glycan chain, judging that a glycan chain is linked to an N-linked glycosylation site in the case different peptide fragments are present among the peptide fragments detected in step (C) and the different peptide fragments are presumed to contain an N-linked glycosylation site or amino acid residue adjacent thereto, and/or judging that a glycan chain is not linked to an N-linked glycosylation site in the case identical peptide fragments are present among the peptide fragments detected in step (C) and those identical peptide fragments are presumed to contain an N-linked glycosylation site.

2. The method according to claim 1, wherein step (A) is carried out using a peptide N-glycanase having deamidase activity.

3. The method according to claim 2, wherein the peptide N-glycanase having deamidase activity is peptide N-glycanase F or peptide N-glycanase A.

4. The method according to claim 1, wherein step (B) is carried out using an endo-type peptidase that acts by specifically recognizing an aspartic acid residue.

5. The method according to claim 4, wherein the endo-type peptidase that acts by specifically recognizing an aspartic acid residue is Asp-N or Glu-C.

6. The method according to claim 1, wherein the detection in step (C) is carried out using a mass spectrometer.

7. A method for detecting a site in a glycoprotein where an N-linked glycan chain is linked by using the method described in claim 1 and determining the proportion of N-linked glycan chain linked from signal strength at the time of detection.

8. A method for detecting a glycoprotein for which the site where an N-linked glycan chain is linked or the proportion of that addition has changed, comprising determining the sites where an N-linked glycan chain is linked, or the proportion thereof that have been linked, for a plurality of samples using the method according to claim 1, and comparing those results.

9. A glycoprotein detected using the method according to claim 8, in which the site where an N-linked glycan chain is linked or the proportion of that addition differs in a comparison between a sample obtained from a patient with a disease and a sample obtained from a healthy individual.

10. A method for detecting a disease, comprising determining the site where an N-linked glycan chain is linked or the proportion of that addition in the glycoprotein according to claim 9 that is present in a sample.

11. A method for determining the site where an N-linked glycan chain is linked or the proportion of that addition in a glycoprotein present in a pharmaceutical by using the method according to claim 1.

* * * * *

SEQUENCE LISTING

```
<160> NUMBER OF SEQ ID NOS: 29

<210> SEQ ID NO 1
<211> LENGTH: 468
<212> TYPE: DNA
<213> ORGANISM: Homo sapiens
```

-continued

```
<220> FEATURE:
<221> NAME/KEY: CDS
<222> LOCATION: (1)..(468)
<220> FEATURE:
<221> NAME/KEY: mat_peptide
<222> LOCATION: (85)..(468)

<400> SEQUENCE: 1 atg gct ctg gag aag tct ctt gtc cgg ctc ctt ctg ctt gtc ctg ata      48
Met Ala Leu Glu Lys Ser Leu Val Arg Leu Leu Leu Leu Val Leu Ile
        -25                 -20                 -15 ctg ctg gtg ctg ggc tgg gtc cag cct tcc ctg ggc aag gaa tcc cgg      96
Leu Leu Val Leu Gly Trp Val Gln Pro Ser Leu Gly Lys Glu Ser Arg
        -10                  -5              -1   1 gcc aag aaa ttc cag cgg cag cat atg gac tca gac agt tcc ccc agc     144
Ala Lys Lys Phe Gln Arg Gln His Met Asp Ser Asp Ser Ser Pro Ser
  5              10                  15                  20 agc tcc tcc acc tac tgt aac caa atg atg agg cgg cgg aat atg aca     192
Ser Ser Ser Thr Tyr Cys Asn Gln Met Met Arg Arg Arg Asn Met Thr
                25                  30                  35 cag ggg cgg tgc aaa cca gtg aac acc ttt gtg cac gag ccc ctg gta     240
Gln Gly Arg Cys Lys Pro Val Asn Thr Phe Val His Glu Pro Leu Val
            40                  45                  50 gat gtc cag aat gtc tgt ttc cag gaa aag gtc acc tgc aag aac ggg     288
Asp Val Gln Asn Val Cys Phe Gln Glu Lys Val Thr Cys Lys Asn Gly
        55                  60                  65 cag ggc aac tgc tac aag agc aac tcc agc atg cac atc aca gac tgc     336
Gln Gly Asn Cys Tyr Lys Ser Asn Ser Ser Met His Ile Thr Asp Cys
    70                  75                  80 cgc ctg aca aac ggc tcc agg tac ccc aac tgt gca tac cgg acc agc     384
Arg Leu Thr Asn Gly Ser Arg Tyr Pro Asn Cys Ala Tyr Arg Thr Ser
85                  90                  95                 100 ccg aag gag aga cac atc att gtg gcc tgt gaa ggg agc cca tat gtg     432
Pro Lys Glu Arg His Ile Ile Val Ala Cys Glu Gly Ser Pro Tyr Val
                105                 110                 115 cca gtc cac ttt gat gct tct gtg gag gac tct acc                     468
Pro Val His Phe Asp Ala Ser Val Glu Asp Ser Thr
                120                 125

<210> SEQ ID NO 2
<211> LENGTH: 156
<212> TYPE: PRT
<213> ORGANISM: Homo sapiens

<400> SEQUENCE: 2

Met Ala Leu Glu Lys Ser Leu Val Arg Leu Leu Leu Leu Val Leu Ile
        -25                 -20                 -15

Leu Leu Val Leu Gly Trp Val Gln Pro Ser Leu Gly Lys Glu Ser Arg
        -10                  -5              -1   1

Ala Lys Lys Phe Gln Arg Gln His Met Asp Ser Asp Ser Ser Pro Ser
  5              10                  15                  20

Ser Ser Ser Thr Tyr Cys Asn Gln Met Met Arg Arg Arg Asn Met Thr
                25                  30                  35

Gln Gly Arg Cys Lys Pro Val Asn Thr Phe Val His Glu Pro Leu Val
            40                  45                  50

Asp Val Gln Asn Val Cys Phe Gln Glu Lys Val Thr Cys Lys Asn Gly
        55                  60                  65

Gln Gly Asn Cys Tyr Lys Ser Asn Ser Ser Met His Ile Thr Asp Cys
    70                  75                  80

Arg Leu Thr Asn Gly Ser Arg Tyr Pro Asn Cys Ala Tyr Arg Thr Ser
```

```
                85                  90                  95                 100
Pro Lys Glu Arg His Ile Ile Val Ala Cys Glu Gly Ser Pro Tyr Val
                    105                 110                 115
Pro Val His Phe Asp Ala Ser Val Glu Asp Ser Thr
            120                 125

<210> SEQ ID NO 3
<211> LENGTH: 128
<212> TYPE: PRT
<213> ORGANISM: Artificial sequence
<220> FEATURE:
<223> OTHER INFORMATION: Synthetic RNase 1 mutated sequence

<400> SEQUENCE: 3

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
                20                  25                  30

Arg Asp Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
        50                  55                  60

Cys Lys Asn Gly Gln Gly Asn Cys Tyr Lys Ser Asp Ser Ser Met His
65                  70                  75                  80

Ile Thr Asp Cys Arg Leu Thr Asp Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

<210> SEQ ID NO 4
<211> LENGTH: 13
<212> TYPE: PRT
<213> ORGANISM: Artificial sequence
<220> FEATURE:
<223> OTHER INFORMATION: Synthetic RNase 1 partial sequence

<400> SEQUENCE: 4

Lys Glu Ser Arg Ala Lys Lys Phe Gln Arg Gln His Met
1               5                   10

<210> SEQ ID NO 5
<211> LENGTH: 37
<212> TYPE: PRT
<213> ORGANISM: Artificial sequence
<220> FEATURE:
<223> OTHER INFORMATION: Synthetic RNase 1 partial sequence

<400> SEQUENCE: 5

Asp Ser Ser Pro Ser Ser Ser Ser Thr Tyr Cys Asn Gln Met Met Arg
1               5                   10                  15

Arg Arg Asn Met Thr Gln Gly Arg Cys Lys Pro Val Asn Thr Phe Val
                20                  25                  30

His Glu Pro Leu Val
        35

<210> SEQ ID NO 6
<211> LENGTH: 30
<212> TYPE: PRT
<213> ORGANISM: Artificial sequence
```

```
<220> FEATURE:
<223> OTHER INFORMATION: Synthetic RNase 1 partial sequence

<400> SEQUENCE: 6

Asp Val Gln Asn Val Cys Phe Gln Glu Lys Val Thr Cys Lys Asn Gly
1               5                   10                  15

Gln Gly Asn Cys Tyr Lys Ser Asn Ser Ser Met His Ile Thr
            20                  25                  30

<210> SEQ ID NO 7
<211> LENGTH: 38
<212> TYPE: PRT
<213> ORGANISM: Artificial sequence
<220> FEATURE:
<223> OTHER INFORMATION: Synthetic RNase 1 partial sequence

<400> SEQUENCE: 7

Asp Cys Arg Leu Thr Asn Gly Ser Arg Tyr Pro Asn Cys Ala Tyr Arg
1               5                   10                  15

Thr Ser Pro Lys Glu Arg His Ile Ile Val Ala Cys Glu Gly Ser Pro
            20                  25                  30

Tyr Val Pro Val His Phe
        35

<210> SEQ ID NO 8
<211> LENGTH: 5
<212> TYPE: PRT
<213> ORGANISM: Artificial sequence
<220> FEATURE:
<223> OTHER INFORMATION: Synthetic RNase 1 partial sequence

<400> SEQUENCE: 8

Asp Ala Ser Val Glu
1               5

<210> SEQ ID NO 9
<211> LENGTH: 18
<212> TYPE: PRT
<213> ORGANISM: Artificial sequence
<220> FEATURE:
<223> OTHER INFORMATION: Synthetic Mutated RNase 1 partial sequence

<400> SEQUENCE: 9

Asp Ser Ser Pro Ser Ser Ser Ser Thr Tyr Cys Asn Gln Met Met Arg
1               5                   10                  15

Arg Arg

<210> SEQ ID NO 10
<211> LENGTH: 19
<212> TYPE: PRT
<213> ORGANISM: Artificial sequence
<220> FEATURE:
<223> OTHER INFORMATION: Synthetic Mutated RNase 1 partial sequence

<400> SEQUENCE: 10

Asp Met Thr Gln Gly Arg Cys Lys Pro Val Asn Thr Phe Val His Glu
1               5                   10                  15

Pro Leu Val

<210> SEQ ID NO 11
<211> LENGTH: 23
<212> TYPE: PRT
<213> ORGANISM: Artificial sequence
<220> FEATURE:
```

<223> OTHER INFORMATION: Synthetic Mutated RNase 1 partial sequence

<400> SEQUENCE: 11

Asp Val Gln Asn Val Cys Phe Gln Glu Lys Val Thr Cys Lys Asn Gly
1               5                   10                  15

Gln Gly Asn Cys Tyr Lys Ser
            20

<210> SEQ ID NO 12
<211> LENGTH: 7
<212> TYPE: PRT
<213> ORGANISM: Artificial sequence
<220> FEATURE:
<223> OTHER INFORMATION: Synthetic Mutated RNase 1 partial sequence

<400> SEQUENCE: 12

Asp Ser Ser Met His Ile Thr
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic Mutated RNase 1 partial sequence

<400> SEQUENCE: 13

Asp Cys Arg Leu Thr
1               5

<210> SEQ ID NO 14
<211> LENGTH: 33
<212> TYPE: PRT
<213> ORGANISM: Artificial sequence
<220> FEATURE:
<223> OTHER INFORMATION: Synthetic Mutated RNase 1 partial sequence

<400> SEQUENCE: 14

Asp Gly Ser Arg Tyr Pro Asn Cys Ala Tyr Arg Thr Ser Pro Lys Glu
1               5                   10                  15

Arg His Ile Ile Val Ala Cys Glu Gly Ser Pro Tyr Val Pro Val His
            20                  25                  30

Phe

<210> SEQ ID NO 15
<211> LENGTH: 5
<212> TYPE: PRT
<213> ORGANISM: Artificial sequence
<220> FEATURE:
<223> OTHER INFORMATION: Synthetic RNase 1 partial sequence

<400> SEQUENCE: 15

Glu Ser Arg Ala Lys
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic RNase 1 partial sequence

<400> SEQUENCE: 16

Phe Gln Arg Gln His Met
1               5

```
<210> SEQ ID NO 17
<211> LENGTH: 10
<212> TYPE: PRT
<213> ORGANISM: Artificial sequence
<220> FEATURE:
<223> OTHER INFORMATION: Synthetic RNase 1 partial sequence

<400> SEQUENCE: 17

Asp Val Gln Asn Val Cys Phe Gln Glu Lys
1               5                   10

<210> SEQ ID NO 18
<211> LENGTH: 4
<212> TYPE: PRT
<213> ORGANISM: Artificial sequence
<220> FEATURE:
<223> OTHER INFORMATION: Synthetic RNase 1 partial sequence

<400> SEQUENCE: 18

Val Thr Cys Lys
1

<210> SEQ ID NO 19
<211> LENGTH: 8
<212> TYPE: PRT
<213> ORGANISM: Artificial sequence
<220> FEATURE:
<223> OTHER INFORMATION: Synthetic RNase 1 partial sequence

<400> SEQUENCE: 19

Asn Gly Gln Gly Asn Cys Tyr Lys
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic RNase 1 partial sequence

<400> SEQUENCE: 20

Ser Asn Ser Ser Met His Ile Thr
1               5

<210> SEQ ID NO 21
<211> LENGTH: 20
<212> TYPE: PRT
<213> ORGANISM: Artificial sequence
<220> FEATURE:
<223> OTHER INFORMATION: Synthetic RNase 1 partial sequence

<400> SEQUENCE: 21

Asp Cys Arg Leu Thr Asn Gly Ser Arg Tyr Pro Asn Cys Ala Tyr Arg
1               5                   10                  15

Thr Ser Pro Lys
            20

<210> SEQ ID NO 22
<211> LENGTH: 18
<212> TYPE: PRT
<213> ORGANISM: Artificial sequence
<220> FEATURE:
<223> OTHER INFORMATION: Synthetic RNase 1 partial sequence

<400> SEQUENCE: 22
```

-continued

```
Glu Arg His Ile Ile Val Ala Cys Glu Gly Ser Pro Tyr Val Pro Val
1               5                   10                  15

His Phe

<210> SEQ ID NO 23
<211> LENGTH: 15
<212> TYPE: PRT
<213> ORGANISM: Artificial sequence
<220> FEATURE:
<223> OTHER INFORMATION: Synthetic Mutated RNase 1 partial sequence

<400> SEQUENCE: 23

Asn Gly Ser Arg Tyr Pro Asn Cys Ala Tyr Arg Thr Ser Pro Lys
1               5                   10                  15

<210> SEQ ID NO 24
<211> LENGTH: 7
<212> TYPE: PRT
<213> ORGANISM: Artificial sequence
<220> FEATURE:
<223> OTHER INFORMATION: Synthetic RNase 1 partial sequence

<400> SEQUENCE: 24

Lys Phe Gln Arg Gln His Met
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic RNase 1 partial sequence

<400> SEQUENCE: 25

Lys Phe Gln Arg Gln His Met Asp Ser
1               5

<210> SEQ ID NO 26
<211> LENGTH: 16
<212> TYPE: PRT
<213> ORGANISM: Artificial sequence
<220> FEATURE:
<223> OTHER INFORMATION: Synthetic RNase 1 partial sequence

<400> SEQUENCE: 26

Asn Gly Gln Gly Asn Cys Tyr Lys Ser Asn Ser Ser Met His Ile Thr
1               5                   10                  15

<210> SEQ ID NO 27
<211> LENGTH: 14
<212> TYPE: PRT
<213> ORGANISM: Artificial sequence
<220> FEATURE:
<223> OTHER INFORMATION: Synthetic RNase 1 partial sequence

<400> SEQUENCE: 27

Glu Ser Arg Ala Lys Lys Phe Gln Arg Gln His Met Asp Ser
1               5                   10

<210> SEQ ID NO 28
<211> LENGTH: 143
<212> TYPE: PRT
<213> ORGANISM: Homo sapiens

<400> SEQUENCE: 28

Gln Asp Pro Tyr Val Lys Glu Ala Glu Asn Leu Lys Lys Tyr Phe Asn
```

-continued

```
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 29
<211> LENGTH: 17
<212> TYPE: PRT
<213> ORGANISM: Artificial sequence
<220> FEATURE:
<223> OTHER INFORMATION: Synthetic interferon gamma partial sequence
      with substitution

<400> SEQUENCE: 29

Asp Asp Gly Thr Leu Phe Leu Gly Ile Leu Lys Asn Trp Lys Glu Glu
1               5                   10                  15

Ser
```